US011589833B2

(12) United States Patent
Toyoda et al.

(10) Patent No.: US 11,589,833 B2
(45) Date of Patent: Feb. 28, 2023

(54) IMAGING SYSTEM AND CONTROL METHOD FOR IMAGING SYSTEM

(71) Applicant: Olympus Corporation, Hachioji (JP)

(72) Inventors: Tetsuya Toyoda, Hachioji (JP); Masaru Ikeda, Fujimi (JP); Hideaki Yoshida, Hachioji (JP); Kazuhiko Osa, Hachioji (JP); Osamu Nonaka, Sagamihara (JP)

(73) Assignee: Olympus Corporation, Tokyo (JP)

( * ) Notice: Subject to any disclaimer, the term of this patent is extended or adjusted under 35 U.S.C. 154(b) by 545 days.

(21) Appl. No.: 16/693,205

(22) Filed: Nov. 22, 2019

(65) Prior Publication Data

US 2020/0196968 A1    Jun. 25, 2020

(30) Foreign Application Priority Data

Dec. 21, 2018  (JP) ............................. JP2018-239525

(51) Int. Cl.
*A61B 6/00* (2006.01)
*G06T 1/00* (2006.01)
*G06T 1/60* (2006.01)
*G06T 1/20* (2006.01)
(Continued)

(52) U.S. Cl.
CPC ............ *A61B 6/461* (2013.01); *A61B 5/222* (2013.01); *G06T 1/0007* (2013.01); *G06T 1/20* (2013.01); *G06T 1/60* (2013.01); *A61B 5/24* (2021.01)

(58) Field of Classification Search
None
See application file for complete search history.

(56) References Cited

U.S. PATENT DOCUMENTS 8,323,191 B2 * 12/2012 Bodlaender ............ A61B 5/165
128/923
9,741,119 B2 *  8/2017 Im ............................ H04N 7/183
10,617,351 B2 *  4/2020 Rau ............................ G16Z 99/00
(Continued)

FOREIGN PATENT DOCUMENTS

JP    2018-097605 A    6/2018

OTHER PUBLICATIONS

H. Takatsu, et al, "An Evaluation of the Quantitative Relationship between the Subjective Stress Value and Heart Rate Variability" in the Transaction of the Institute of Electrical engineers of Japan C, vol. 120, internet URL: https://www.jstage.jst.go.jp/article/ieejeiss1987/120/1/120_1_104/_pdf, downloaded on Nov. 22, 2019.

(Continued)

*Primary Examiner* — Anand P Bhatnagar
(74) *Attorney, Agent, or Firm* — John C. Pokotylo; Pokotylo Patent Services

(57) ABSTRACT

An imaging system, comprising a shooting operation interface that operates to form an image of a subject, and a processor that has a bio-information acquisition section and a stress determination section, wherein the bio-information acquisition section acquires bio-information of an operator when, during shooting awaiting action where an instant for acquiring still images is awaited, the shooting operation interface is operated, and the stress determination section determines stress conditions that shooting actions place on the operator based on the bio-information that has been acquired using the bio-information acquisition section.

13 Claims, 18 Drawing Sheets

(51) Int. Cl.
  *A61B 5/22* (2006.01)
  *A61B 5/24* (2021.01)

(56) References Cited

U.S. PATENT DOCUMENTS

| | | | |
|---|---|---|---|
| 11,157,906 B1* | 10/2021 | Smith | G06Q 20/405 |
| 2010/0165076 A1 | 7/2010 | Vau | |
| 2014/0372133 A1* | 12/2014 | Austrum | G16H 50/30 705/2 |
| 2020/0014848 A1* | 1/2020 | Gove | G06F 3/01 |
| 2020/0390328 A1* | 12/2020 | Toth | A61B 5/163 |
| 2021/0361208 A1* | 11/2021 | Lee | A61B 5/14546 |
| 2021/0378414 A1* | 12/2021 | Fernandes | A47C 27/065 |
| 2022/0030182 A1* | 1/2022 | Park | H04N 5/2251 |
| 2022/0047223 A1* | 2/2022 | Gondi | G16H 50/20 |
| 2022/0093001 A1* | 3/2022 | Szkatulski | G06N 20/20 |

OTHER PUBLICATIONS

"Moderate Stress Contributes to Brain Revitalization" on the Japan Preventative Association of Life-Style related Disease home page, internet URL: http://www.seikatsusyukanbyo.com/calendar/2013/002308.php, downloaded on Nov. 22, 2019.

"The Science of Stress and Autonomous Nerves", internet URL: http://hclab.sakura.ne.jp/stress_novice_hartrate.html, downloaded on Nov. 22, 2019.

Abstract of M. Komazawa, et al, "Evaluation of Heart Rate in Daily Life Based on 10 Million Samples Database," *Global Journal of Health Science*, vol. 9, No. 9 (2017) (COCOLOLO research results have been published in peer-reviewed international academic journals), internet URL: https://www.winfrontier.com/news/2017/07/17/cocololo, downloaded on Nov. 22, 2019.

"Research Relating to measurement and evaluation of Autonomous Nervous Function in Daily Life", internet URL: http://www.lib.kobe-u.ac.jp/repository/thesis2/d1/D1006751.pdf, downloaded on Nov. 8, 2019.

* cited by examiner

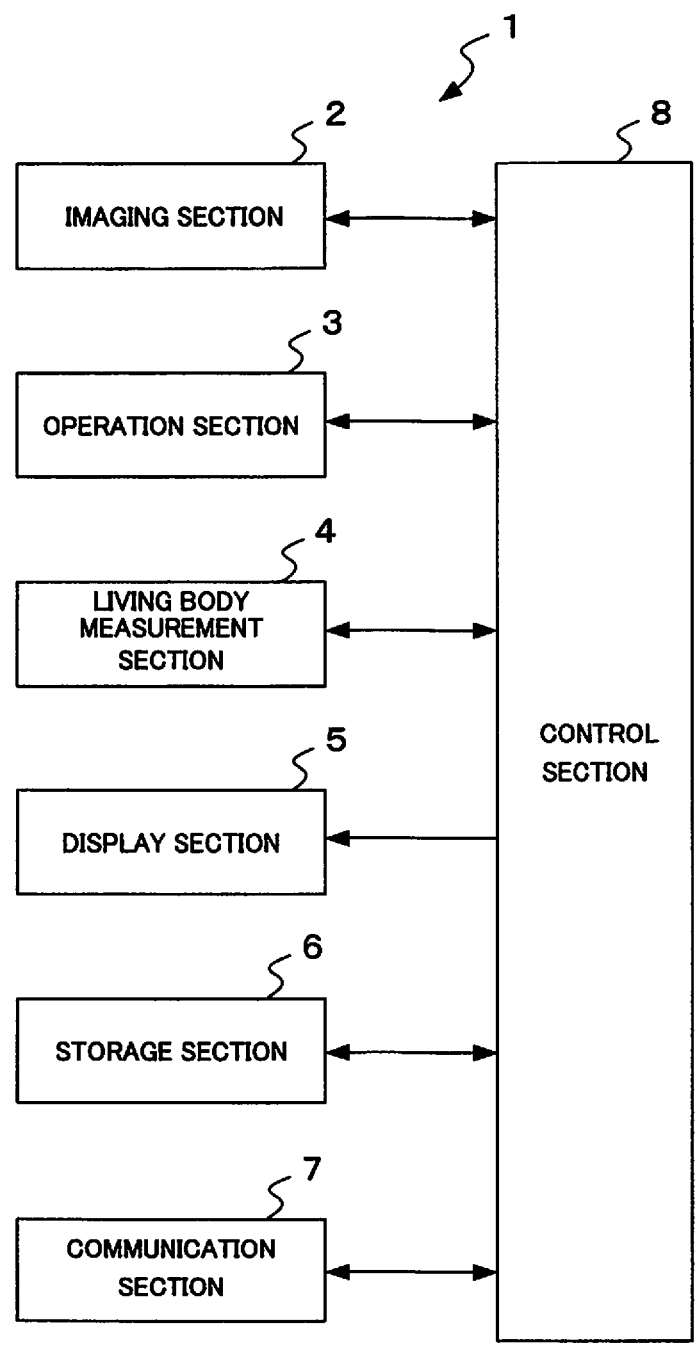

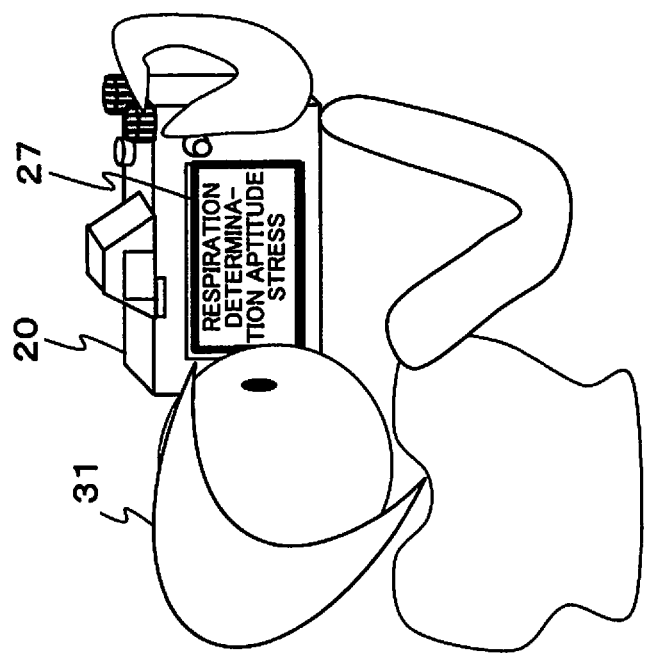
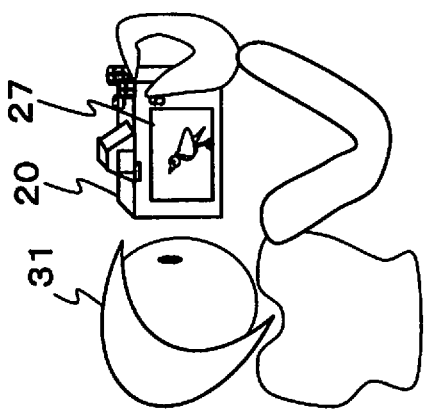
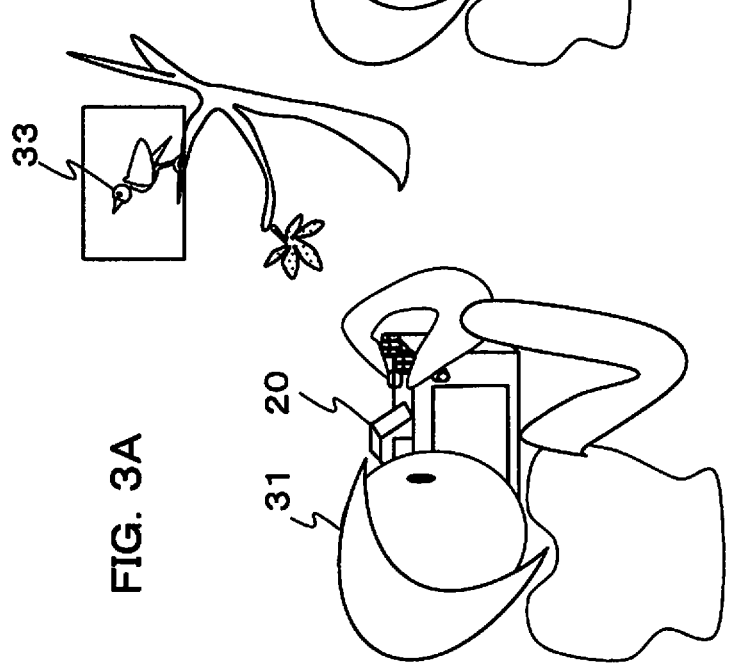

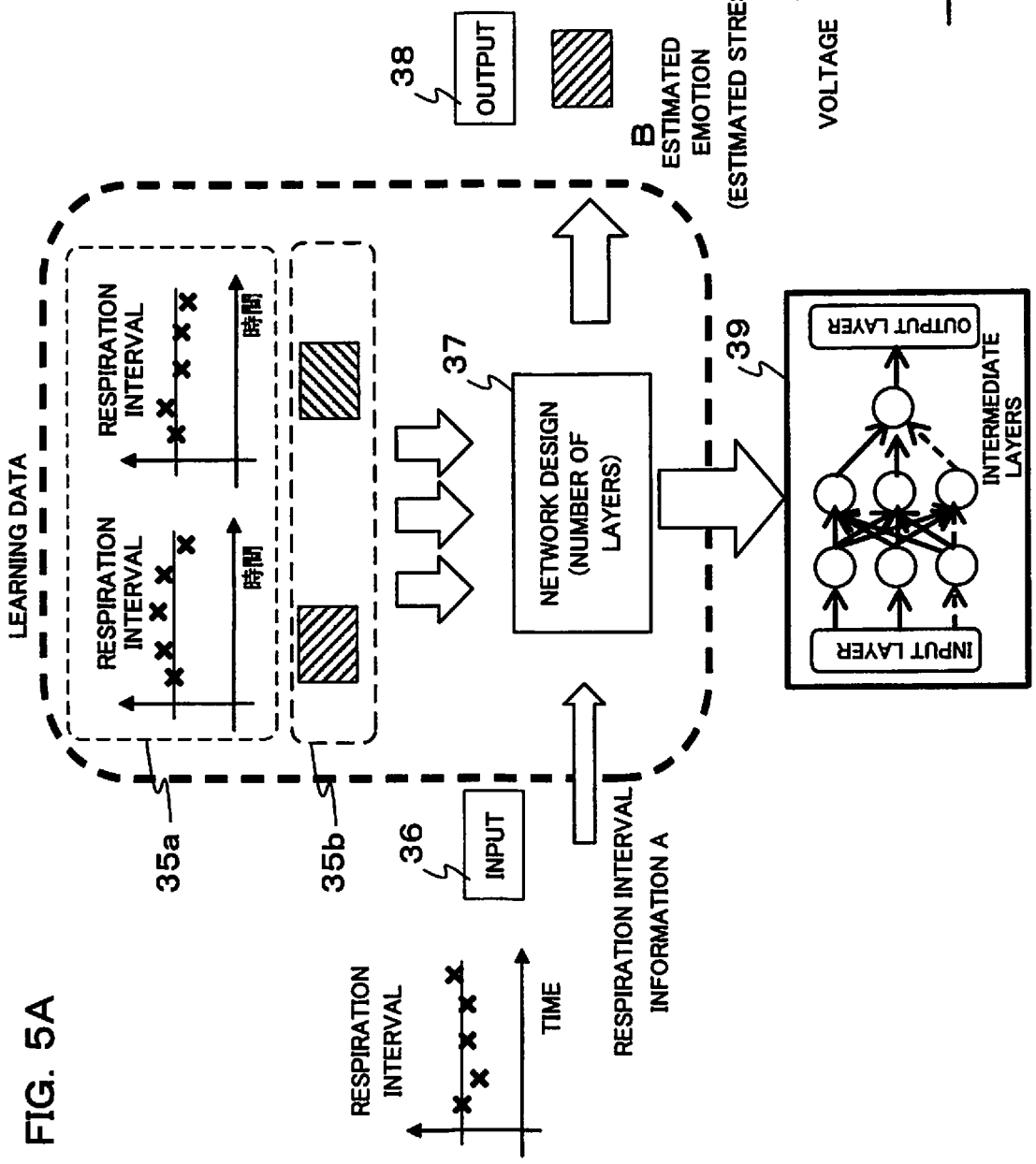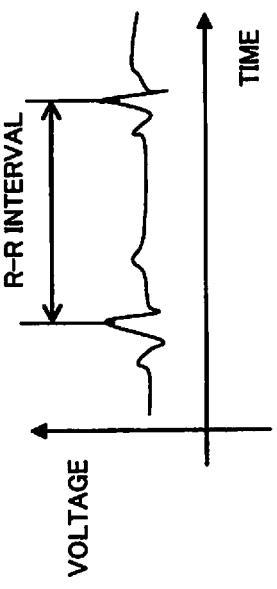

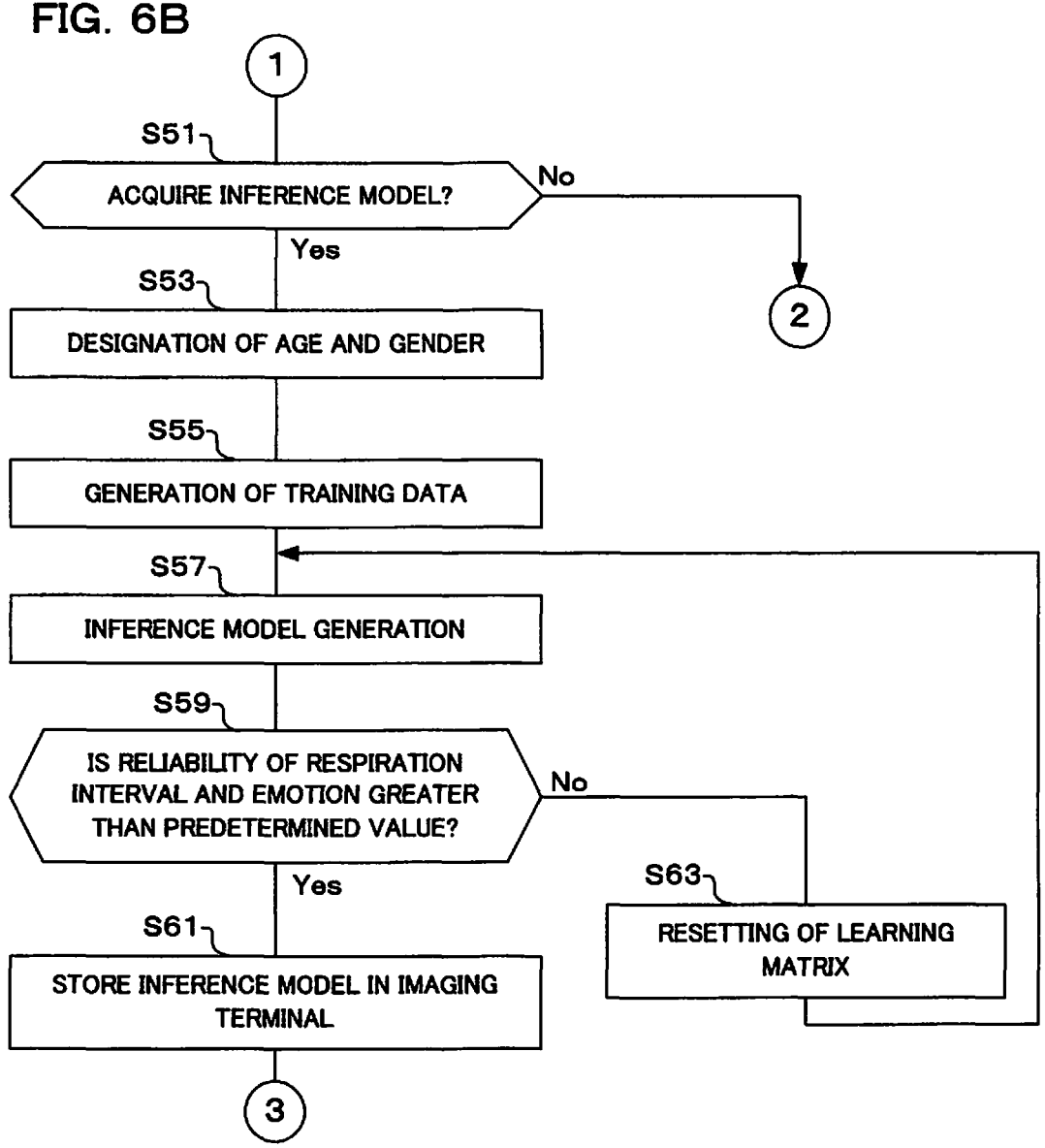

IMAGING SYSTEM AND CONTROL METHOD FOR IMAGING SYSTEM

CROSS-REFERENCE TO RELATED APPLICATIONS

Benefit is claimed, under 35 U.S.C. § 119, to the filing date of prior Japanese Patent Application No. 2018-239525 filed on Dec. 21, 2018. This application is expressly incorporated herein by reference. The scope of the present invention is not limited to any requirements of the specific embodiments described in the application.

BACKGROUND OF THE INVENTION

1. Field of the Invention

The present invention relates to a proposed device that notifies the fact that behavior that contributes to health is being performed, and a control method for the device. Specifically, the present invention relates to an imaging system that measures bio-information of a user while they are performing shooting actions with an imaging device, and is capable of display based on the measurement results so that using the device becomes more enjoyable, and relates to a control method for the imaging system.

2. Description of the Related Art

There is strong interest in individual health, and a terminal device that performs list display of contents related to health has been proposed (refer, for example, to Japanese patent laid-open No. 2018-097605 (hereafter referred to as patent publication 1)). Also, conventionally it has been proposed to examine shooting etc. in which bio-information is reflected, and to provide temperature sensors in mobile terminals, and detect that a photographer has placed their finger on a release button based on this sensor output (refer, for example, to Japanese patent laid-open No. 2010-520688 (hereafter referred to as patent publication 2)).

Also, in recent years changes in physiological response when suffering from psychological stress, such as heart rate, pulse waves, peripheral skin temperature, respiration, skin electrical activity, eye movement, brain waves, etc. are known. For example, taking waveform of an electrocardiogram as an example, an interval between R waves where maximum amplitude of an electrocardiogram waveform is large is called an R-R interval. The R-R interval moves with an average value as a center, and this movement is affected by state of a mental activities. This means that there is a possibility of being able to evaluate psychological stress from aspects of heart rate variability (refer, for example, to the "Considerations regarding evaluation of psychological stress using heart rate variability" in the Transactions of the Institute of Electrical engineers of Japan C, Vol 120, internet URL:https://www.jstage.jst.go.jp/article/ieejeiss1987/120/1/120_1_10 4/_pdf (hereafter referred to as non-patent publication 1)). There is also a report that if sudden stress is in moderation nerve cells proliferate significantly, contributing to improvement in memory (refer to the article "Moderate Stress Contributes to Brain Revitalisation" on the Japan Preventative Association of Life-style related Disease home page, internet URL: http://www.seikatsusyukanbyo.com/calendar/2013/002308.php (hereafter referred to as non-patent publication 2)).

It is also possible to detect emotional states (stress condition) using respiration, as well as heart rate. Respiration and stress condition are related to autonomous nerve functions, and respiration and heart rate fluctuating in synchronism has been observed (refer, for example, to "The Science of Stress and Autonomous Nerves", internet URL: http://hclab.sakura.ne.jp/stress_novice_hartrate.html (hereafter referred to as non-patent publication 3)). Further, an application has been proposed that detects fluctuations in heart rate from blood intensity changes by pressing a finger against a smartphone for about 30 seconds. Using this application, research results relating to heart rate in everyday life are also being reported (refer, for example, to "COCOLOLO research results have been published in peer-reviewed international academic journals", internet URL: https://www.winfrontier.com/news/2017/07/17/cocololo (hereafter referred to as non-patent publication 4), and "Research Relating to measurement and evaluation of Autonomous Nervous Function in Daily Life", internet URL: http://www.lib.kobe-u.ac.jp/repository/thesis2/d1/D1006751.pdf (hereafter referred to as non-patent publication 5)).

It is known that moderate stress is also good for health. Activities relating to various businesses and hobbies may subconsciously contribute to maintaining health, or may impede health maintenance, but many people live their daily live without being conscious of this. For example, there are cameramen who are perform photography as a profession, and also many people who are interested in photography without it being their profession. At the time of photography, in order for a user to take photographs that they like, they will focus on shooting by walking about looking for suitable subjects, trying various compositions, adjusting exposure etc. which would induce various stresses. However, even if stress in induced, if this stress is moderate it is good for health. Users are not generally aware of the fact that moderate stress brought about by concentrating on photography contributes to health. Further, if photographs that have been taken while under stress are very well liked by the user, it can be considered that they also relieve stress and are good for health. This is not limited to photography, and can be said to apply to all daily activities with positive actions, such as household chores, child rearing and volunteer work, regardless of whether it is as a profession or as a hobby.

As one example of detecting a user's activities, it is been proposed to provide a temperature sensor in the camera, and determine whether or not there is a shooting preparation state (refer to patent publication 2). However, an imaging device that makes the fact that performing an activity contributes to health known has not been proposed. Also, an imaging device that can display health information while shooting actions are being performed has not been proposed.

SUMMARY OF THE INVENTION

The present invention provides a device that can detect, and make known, the fact that performing an activity contributes to health, which a user may have been unaware of, and a control method for such a device.

An imaging system of a first aspect of the present invention comprises a shooting operation interface that operates to form an image of a subject, and a processor that has a bio-information acquisition section and a stress determination section, wherein the bio-information acquisition section acquires bio-information of an operator when, during a shooing awaiting action where an instant for acquiring still image is awaited, the shooting operation interface is operated, and the stress determination section determines stress conditions that shooting actions place on the operator based on the bio-information that has been acquired using the bio-information acquisition section.

A control method for an imaging system of a second aspect of the present invention comprises imaging a subject, acquiring bio-information of an operator while photography actions are being performed, and determining stress conditions placed on the operator by the shooting actions, based on the bio-information.

A server of a third aspect of the present invention comprises, a communication circuit for performing communication with a portable information terminal, a database that stores health check results of the operator of the portable information terminal, and a processor, wherein the processor (1) receives bio-information of the operator from the portable information terminal via the communication circuit, (2) determines causes of stress based on the relevancy between the bio-information that has been received and the health check results that have been stored in the database, and (3) generates advice based on the causes of stress.

BRIEF DESCRIPTION OF THE DRAWINGS

FIG. 1B is a block diagram showing the structure of the photography system of the first embodiment of the present invention.

FIG. 3A to FIG. 3C are drawings describing a usage method for the imaging terminal of the second embodiment of the present invention.

FIG. 5A and FIG. 5B are drawings describing generation of an inference model for detecting bio-information, in the imaging terminal of the second embodiment of the present invention.

FIG. 6A to FIG. 6C are flowcharts showing operation of an imaging terminal of the second embodiment of the present invention.

DETAILED DESCRIPTION OF THE PREFERRED EMBODIMENTS

Figure 1A:
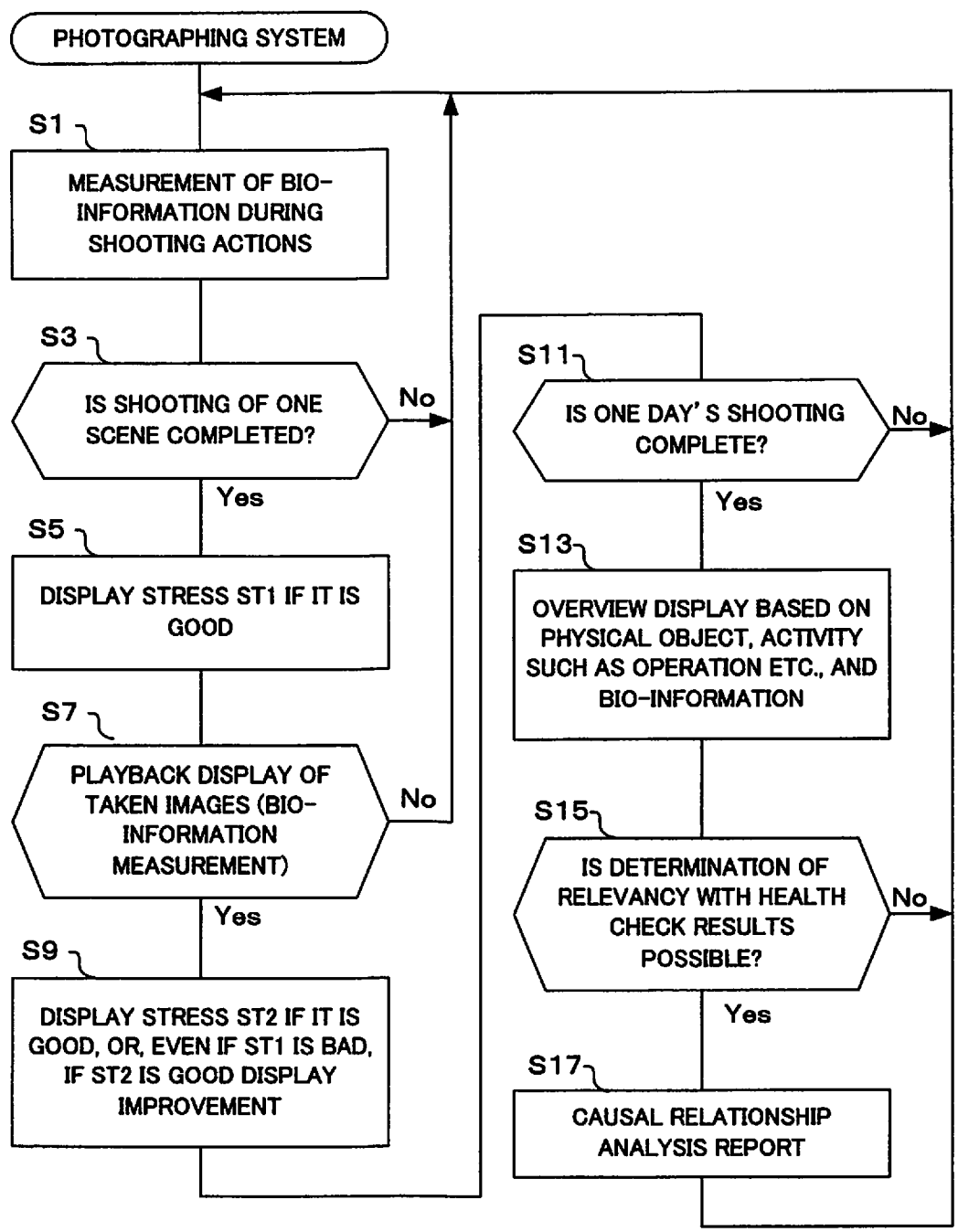
FIG. 1A is a flowchart showing operation of a photography system of a first embodiment of the present invention.

A system that includes the device of an embodiment of the present invention will be described using an example of camera functions that are easy to incorporate into a mobile terminal. It should be noted that a camera may be a standalone type camera, and may also be a system that includes a server etc. A stand alone type of camera can be considered as a system formed from an amalgamation of various devices (functions), and in the case where a camera and server are associated also, it is possible to consider a system that is a combination of these devices. As an exemplification of a camera here, information that is handled is images, and since various information is included, depending on the situation many actions and operations are related, and when a user uses a camera there are various accompanying activities and so effective information is easy to obtain. There is the advantage that a situation while the user is performing operation can also be readily analyzed from images. There is also the advantage that cameras have high consumer use, and it is easy to obtain information from a great many users. Obviously this application can also be applied to other devices, for example, devices for business use, technical testing equipment etc. An imaging system (imaging device) such as a camera measures bio-information of the user (photographer) during shooting actions. As bio-information there is various information that can be digitized at a medical checkup etc. With this embodiment, relative change is clear and easy to measure in a short time, it is assumed to be at least one among information such as heart rate, respiration, perspiration, eye movement, brain waves, muscle strength etc. Information may be other than that described here, and may also be a plurality of information, and at least one of these bio-information is measured. Recently there are many instances of the users taking pictures of themselves, such as a selfy, and in this case it is also possible to use images of faces that have been taken as required.

If human beings are captured dualistically, they are captured in mental and spiritual states, and in physical states. It is preferable for both mental and physical state to be healthy, and either mental or physical healthiness becoming impaired is linked with emotions and sensations such as pain, anxiety and loss of form, which will affect a person's reason for living, zest for life etc. Also, it is known that as a result of returning to health both the mind and body feel better, and is connected to desire and motivation. A concept that can be applied to both mind and body is stress. Research in this field is advancing for preventing health from being impaired, for maintaining good health research, and for promoting health.

Because of this concept, psychological conditions are reflected in physical conditions, which means that evaluating psychological stress of a user by analyzing appropriate biological signals is suitable for measuring mind and body state of a user. In other words, as bio-information that will be determined there is preferably bio-information corresponding to stress. In the Japanese language stress has a negative implication and a positive implication, and here may be used to mean reactions at the time when psychological stress etc. is applied. Since bio-information itself may also represent physical state, physical fatigue and physical change may be estimated together, for example, by determining bio-information.

Also, human beings process many things using information that has been acquired simply by looking. Life is lived by appreciating, observing and recording particular things. Things that have been seen are recorded by drawing picturesquely, writing down using words, etc. Shooting actions using an imaging device are actions that are widespread from the point of view that many people can perform them easily. As well as keeping things that have been seen in a recording, it can be considered to be somewhat close to a person's heart, and shooting actions are backed by a desire to see these later again and tell others. Various information is included in taken images acquired as a result of shooting actions, and also in actions leading up to shooting actions, and a situation where a user is staying, and things such as intentions and interests in that situation, are included. For actions such as shooting, there are cases of going to the trouble of adjusting schedules and traveling a long way. From the viewpoint of this type of feature, an imaging device can be considered to be a device that obtains information that is a mix of activities and behaviors. When going a long way or at the time of an event the user often has a lot of photographic equipment to carry, and information acquisition is possible using various situations. Equipment controllers etc. also require effort, and information according to abundant conditions is acquired.

Specifically, shooting actions can include actions by the user at the time of shooting, using an imaging device, and to describe a series of operations until the user has aimed at and captured a subject, for example, shooting preparation operations to perform determination of subject composition, focusing, and exposure adjustment etc. This also includes an operation to perform photographing by operating a release button etc. Mental activity focused on each of these processes is concentrated. Further, in actual fact, shooting actions are not limited to operations of providing an imaging device and shooting a subject, and operations to move with the imaging device in order to search for an intended subject are included in shooting actions.

Also, among these actions processes that are worth analyzing exist as units, and since psychological and physical stress shows up in each pause and unit of an operation, pauses between each of these units may also be used. In acquiring bio-information it takes time until change arises, and although change is detected accurately it is often not possible to perform analysis in a short time. However, a state where a user is concentrating and aiming at a photographed physical object can be considered as a state that is suitable for detection of bio-information. Having referenced actions being performed with such concentration, it can be said to be a normalized state as a "shooting action", as it were. Specifically, it can be said that comparison and analysis can be performed under the same conditions, which makes them effective. However, although measurement takes time, for a specific moment measurement may be performed based on change in bio-information etc. before and after that moment.

In this way, it is possible to analyze stress information of an operator of a device using change in bio-information. Stress has a close relationship with the state of a user's health. If stress is good stress, it is likely that the state of a person's health will become good, while if stress is intense it is likely that their health will deteriorate. Therefore, if relevancy of stress information and health check results is analyzed based on bio-information it becomes possible to give advice relating to health to the user. Specifically, in a case of taking pictures every day while walking carrying an imaging device such as a camera, stress information is collected without bothering the user, and it is possible to analyze a relationship with state of health.

From the viewpoint of change in the above described bio-information, there is no limitation to shooting actions using a camera, and bio-information also changes at the time of operating various devices that are used by an operator for hobbies and business (for example, a personal computer, game unit, a medical device such as an endoscope, an optical device such as a microscope, and industrial equipment such as machine tools). Specifically, if bio-information changes when a user operates various devices, it is possible to measure psychological and physical stress based on this change. With these type of devices also, similarly to shooting devices like a camera, there are operations that are essential at the time of handling that device, and it is possible to adopt an approach where measurement results are normalized with such essential operations as a reference. Various operations being associated with bio-information is also similar. From the relationship between these operations and bio-information, it also becomes possible to perform analysis etc. such as what type of operations form the basis of stress.

First, operation of an imaging system of a first embodiment of the present invention will be described using the flowchart shown in FIG. 1A and the block diagram shown in FIG. 1B. As shown in FIG. 1B, this imaging system 1 comprises an imaging section 2, operation section 3, living body measurement section 4, display section 5, storage section 6, communication section 7 and control section 8 (including a control processor such as a CPU).

The imaging section 2 comprises a photographing lens, image sensor and imaging circuit (including an imaging control circuit, imaging signal processing circuit etc.), and converts an image that has been formed by the photographing lens to image data. The operation section 3 is an interface for a user to input instructions to the imaging system, and includes operation members such as a release button and power switch etc. If the release button is pressed, a shooting instruction is output to the control section 8.

The living body measurement section 4 has a sensor that measures bio-information of a user, in particular a person who uses the imaging system. As bio-information, as was described previously, information of at least one of heart rate, respiration, perspiration, eye movement, brain waves and muscle strength etc. is measured. It should be noted that the living body measurement section 4 may also be provided within the imaging system. For example, an external unit may be provided with the living body measurements section, and the imaging system may obtain bio-information from the external biological measurement section by means of wireless communication etc.

The display section 5 has a display, and displays a live view image that has been acquired by the imaging section 1, playback images for images that have been stored in the storage section 5, images that have been generated based on bio-information that has been measured by the living body measurement section 4, etc. The storage section 6 stores image data that has been acquired by the imaging section 2 when shooting has been instructed using a release button of the operation section 3. The communication section 7 has a communication circuit for performing communication with an external unit (including a server etc.).

The control section 8 is a processor, may be configured using an ASIC (Application Specific Integrated Circuit), and has a CPU (Central Processor Unit), and performs overall control by controlling each section within the imaging system in accordance with programs that have been stored in nonvolatile memory.

If the flow shown in FIG. 1A is commenced, first bio-information is commenced during shooting actions (S1). In this step a subject is displayed on the display section 5 based on image data that has been acquired by the imaging section 2. The user performs shooting actions such as determining composition, determining focus, and determining exposure, for a photographed object source to be able to take a photograph that they intend to. As was described previously, shooting actions are not limited to actions while preparing for shooting by facing a subject, and may also include actions such as looking for a photographed object and inspection actions for playback of taken images after shooting, etc.

Figure 11:
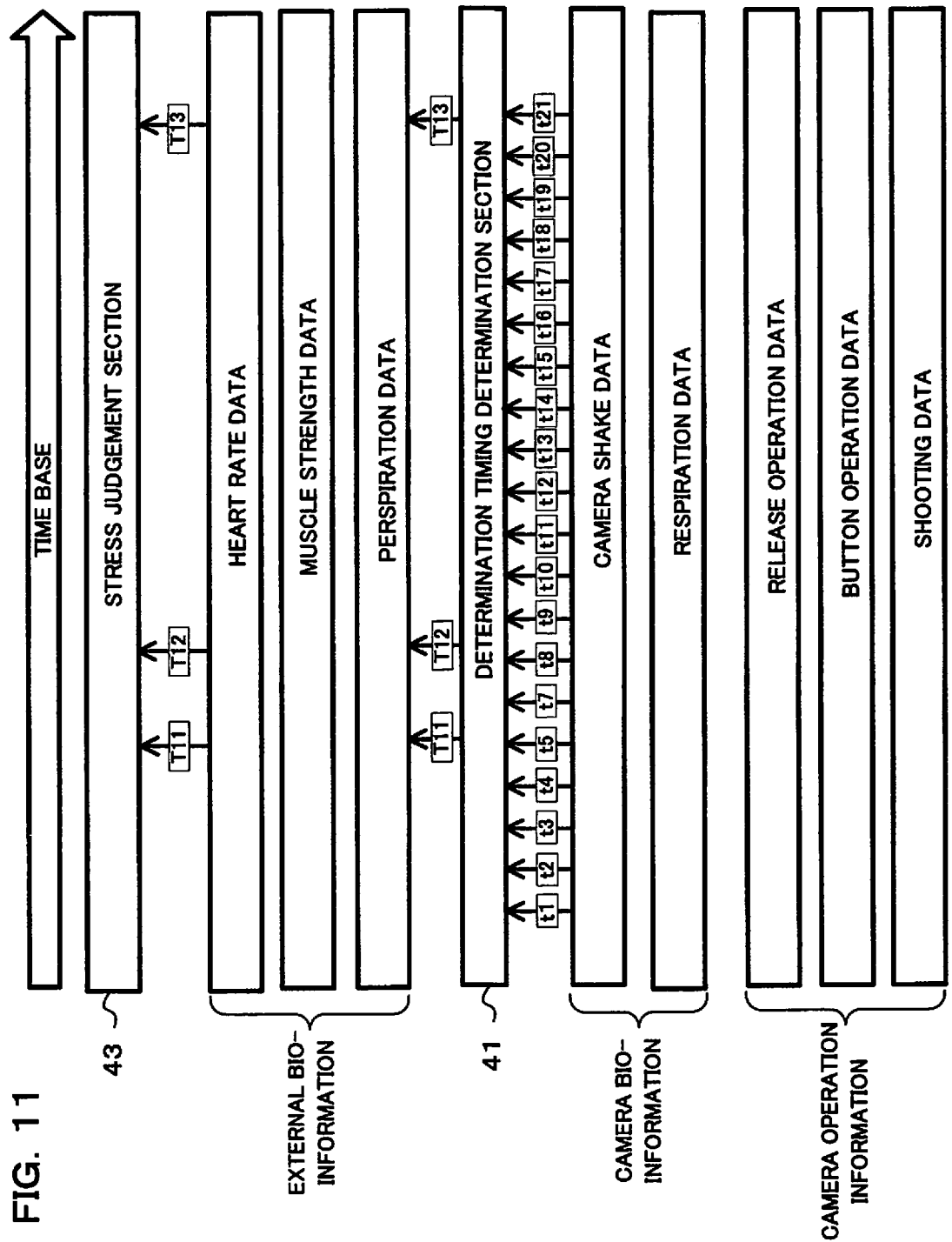
FIG. 11 is a drawing showing one example of timing for performing determination of stress, in each of the embodiments of the present invention.
Figure 12:
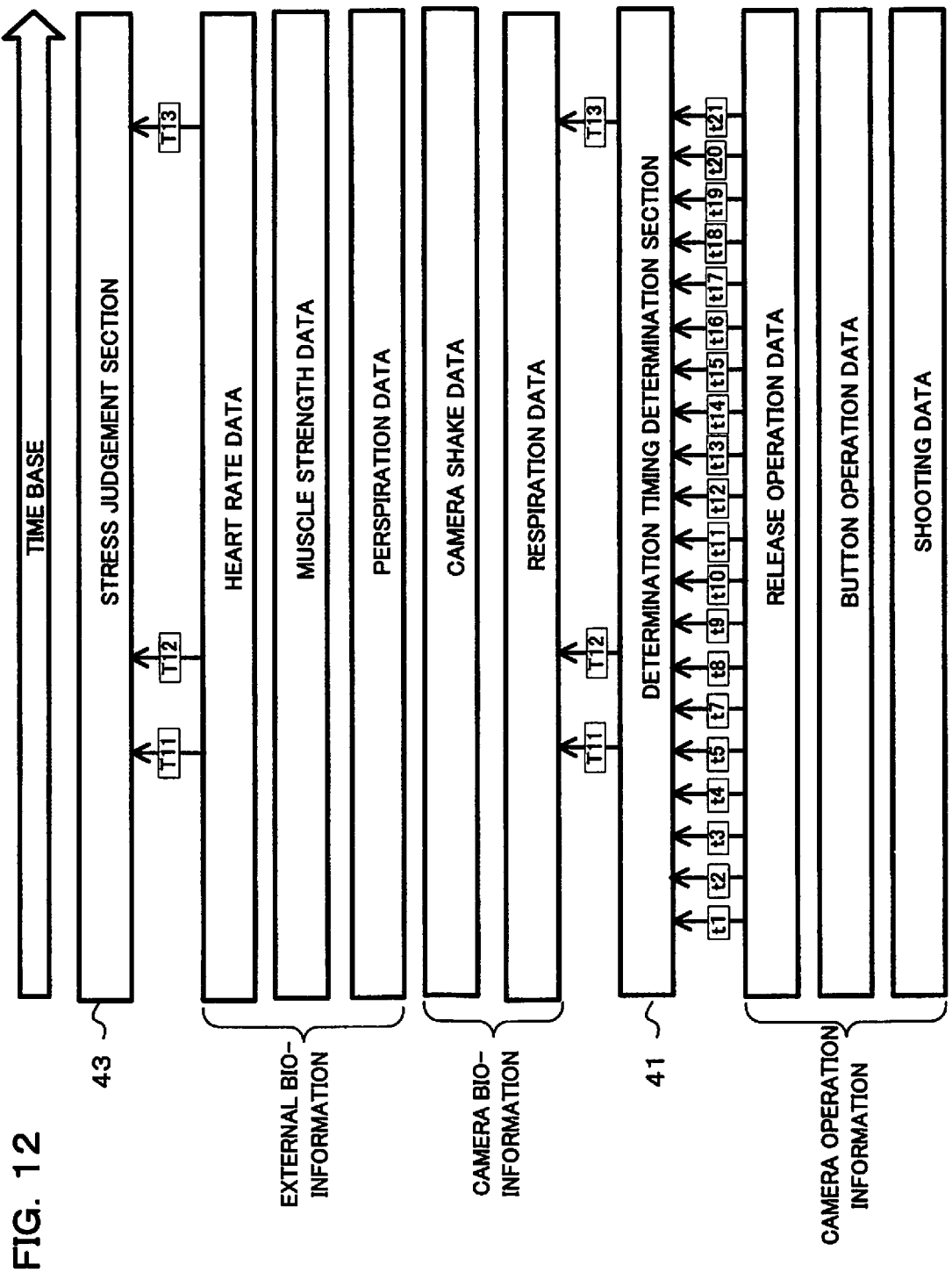
FIG. 12 is a drawing showing a modified example of timing for performing determination of stress, in each of the embodiments of the present invention.

The user performs operation of the imaging device (camera) during shooting actions, and at this time physiological responses such as heart rate, pulse waves, peripheral skin temperature, respiration, skin electrical activity, eye movement, brain waves etc. are detected by sensors provided in the living body measurement section 4 that is provided in the imaging system (refer to FIG. 11 and FIG. 12). It should be noted that in measurement of the bio-information, as was described previously, the imaging device may receive detection results from sensors for bio-information measurement that have been provided externally to the imaging device. For example, bio-information such as heart rate, pulse waves, and respiration rate may be detected by a wristwatch type information terminal, and this information received. Further, bio-information may also be information of a pedometer, GPS etc. From these items of information it is possible to acquire information such as exercise condition and movement information of the user. It should be noted that if detection of bio-information is restricted to at the time of operation for shooting actions etc., it is possible to prevent wasting of electrical power by the living body measurement section. Also, detection timing may be appropriately set so as to prevent power supply consumption.

Next, it is determined whether or not shooting of one scene has been completed (S3). One scene is up until completion of shooting of the subject that the user intends to shoot. For example, one scene is until the user has completed photography by shooting a bird. However, if a single picture of a bird has been taken it may be until completion of a series of photographs. This is because, for example, there may be a case of continuously photographing a bird, and shooting may be performed a number of times with different compositions. The determination here is in a break during a series of photographing operations. A state where a photographed physical object is being focused on and captured in this way is a situation where that action has been referenced, and normalized as a "shooting action" so to speak. This situation is comparatively stable, and it can be said that it is possible to accurately detect bio-information. Specifically, it can be said to be a situation in which comparison and analysis are effective under the same conditions. If the result of determination in step S3 is that shooting for one scene is not completed, step S1 is returned to. Bio-information is repeatedly measured in step S1 until shooting of one scene has been completed.

On the other hand, if the result of determination in step S3 is that shooting for one scene has been completed, next stress ST1 is displayed if it is good (S5). In this step, first the control section 8 determines stress ST1 based on physiological responses of the user such as heart rate, pulse waves, peripheral skin temperature, respiration, skin electrical activity, eye movement, brain waves etc. that have been detected by the living body measurement section 4 during shooting actions. If the result of this determination is that stress ST1 is good, the fact that stress is good is displayed on the display section 5. As was described previously, since an appropriate level of stress is good for health, it is determined whether or not stress is at an appropriate level and not excessive. If the result of this determination is that stress is good, that fact is displayed. A user who sees this display will be encouraged to go out and take photographs.

Next, playback display of taken images is performed (S7). Here, images that were taken at the time of a Yes determination in step S3 are subjected to playback display on the display section 5. In this way it is possible for the user to confirm taken images. Also, together with the user confirming taken images, the living body measurement section 4 performs measurement of bio-information. When the user has confirmed the taken images they will have various feelings, such as whether it was possible to have taken the photograph they wanted to, or whether photographs were not as they intended etc., and this would show up as change in bio-information. By looking at this change in bio-information it is possible to determine stress ST2 of the user. It should be noted that the bio-information measurement of step S7 is performed at the time of playback display of taken images, and so it is possible to restrict measurement time and as a result it is possible to prevent wasting of electrical power by the living body measurement section. If playback display of taken images etc. is not performed in step S7 processing returns to step S1.

Once playback display of taken images has been performed and bio-information has been measured in step S7, next stress ST2 is displayed if it is good, or even if stress ST1 is not good and stress ST2 is good, the fact that stress has improved is displayed (S9). Here, if stress ST2 based on the bio-information that was measured in step S7 is good, the fact that there is good stress is displayed on the display section 5. There may be cases where it is possible to estimate that the user is satisfied with photographs that have been taken.

Also in step S9, if stress ST1 was not good but stress ST2 is good, the fact that stress has improved is displayed on the display section 5. In this case, there may be cases where the user prepared for shooting under stress that was not appropriate, but was able to shoot photographs that they were ultimately sufficiently satisfied with. In this type of case display is performed so as to energize the user and give them a sense of satisfaction.

Next, it is determined whether or not one day's shooting has been completed (S11). Here it is determined whether or not a series of shooting operations has been completed. As a method for this determination photographed objects by the user may be analyzed, determination may be performed simply from time, and the user may manually set completion. If the result of this determination is not completion, processing returns to step S1.

If the result of determination in step S11 is completion, overview display is performed based on physical objects, actions for operations etc., and bio-information (S13). Here, since a series of photographing operations for one day has been completed state of health relating to stress etc. is displayed based on physical object information, action information, and bio-information that has been acquired for that day. For example, the fact that although at the time shooting commenced there was stress, it was found that ultimately there was improvement in stress, is displayed on the display section 5. The user can see change in their own stress accompanying photography by looking at this display. In particular if an improvement in stress was seen, it is possible to be made aware of the utility of photography, and the user will feel better. Although description here has centered on stress, there will obviously be cases where shooting actions will have an effect on blood pressure, blood glucose levels, body weight and body fat etc., and effects on health will be seen. These type of effects may therefore also be displayed from bio-information. When we handle this bio-information by theory of DNB (Dynamical Network Biomarkers) analysis and its application, the display will be able to show the result of the detection of the user's predisease states or the prediction result of some disease for user in cooperation with the control section.

Once overview display has been performed, relevancy of health check results is determined (S15). If the results of a user's medical checkup are stored in the imaging device, or if it is possible to connect to a health management server by means of communication, the control section 8 determines whether or not it is possible to determine relevancy of stress that has been determined by the imaging system and results of the medical checkup. It is also possible to perform determination based not only on stress for that day, but also based on previous shooting achievements, change in measurement results of bio-information etc. and change in previous health check results. If determination is not possible processing returns to step S1.

On the other hand, if the result of determination in step S15 is that it is possible to determine relevancy, a causal relation analysis report is generated (S17). For example, in a case where blood pressure dropped according to the user's health check results, by comparing with previous shooting achievements there may be cases where it is possible to determine that blood pressure dropped as a result of shooting. This causal relation analysis report that has been generated may be displayed on the display section 5 of the imaging system and may be displayed on an external personal computer etc. by means of the communication section 7. It should be noted that a specific example of associating health check results and stress will be described later using FIG. 8. Once a causal relation report has been created, processing returns to step S1.

In this way, with this embodiment a user's bio-information is measured by the living body measurement section 4 during shooting actions. Then based on these measurement results if stress is good the fact that stress is good is displayed on the display section 5, and the user is invigorated so as to have motivation to do more photography.

Also, with this embodiment bio-information is measured by the living body measurement section 4 during shooting preparation and during image confirmation, and if stress has improved the fact that stress has improved is displayed on the display section 5. Further, overview display is also performed when shooting for one day has been completed. As a result of the user looking at the display showing that stress has improved, they will be motivated to perform photography, and photography will become more enjoyable.

Also, with this embodiment, measurement of bio-information by the living body measurement section 4 is performed when specified operation has been performed during shooting preparation and during confirmation of taken images (refer, for example, to S1, S7, FIG. 11 and FIG. 12). Since measurement of bio-information involves significant energy consumption by sensors, it is possible to reduce energy consumption by measuring bio-information in conformity with operation times.

Also, with this embodiment, overview display is performed based on bio-information etc. at a time when shooting is finished for the day (refer to S13). This means that by performing one day shooting it is possible to confirm how stress condition has changed.

Also, with this embodiment, relevancy of health check results of an operator. (user) operating a unit and stress information etc. is determined (refer to S15 and S17). It should be noted that with this embodiment, in the case of good stress the fact that there is good stress is displayed (S5, S9). However, display is not limited to the case of good stress, and in cases such as where a user is subjected to stress that is not good (excessive stress) also, that fact may also be displayed. In this case, it is possible to analyze the good effects on health, or the causes of deterioration in health, using stress information. In a case of taking pictures every day while walking carrying an imaging device such as a camera, stress information is collected without bothering the user, and it is possible to analyze a relationship with state of health.

Next, a second embodiment of the present invention will be described using FIG. 2 to FIG. 6C. This embodiment is an example more specifically showing the imaging device of the first embodiment.

Figure 2:
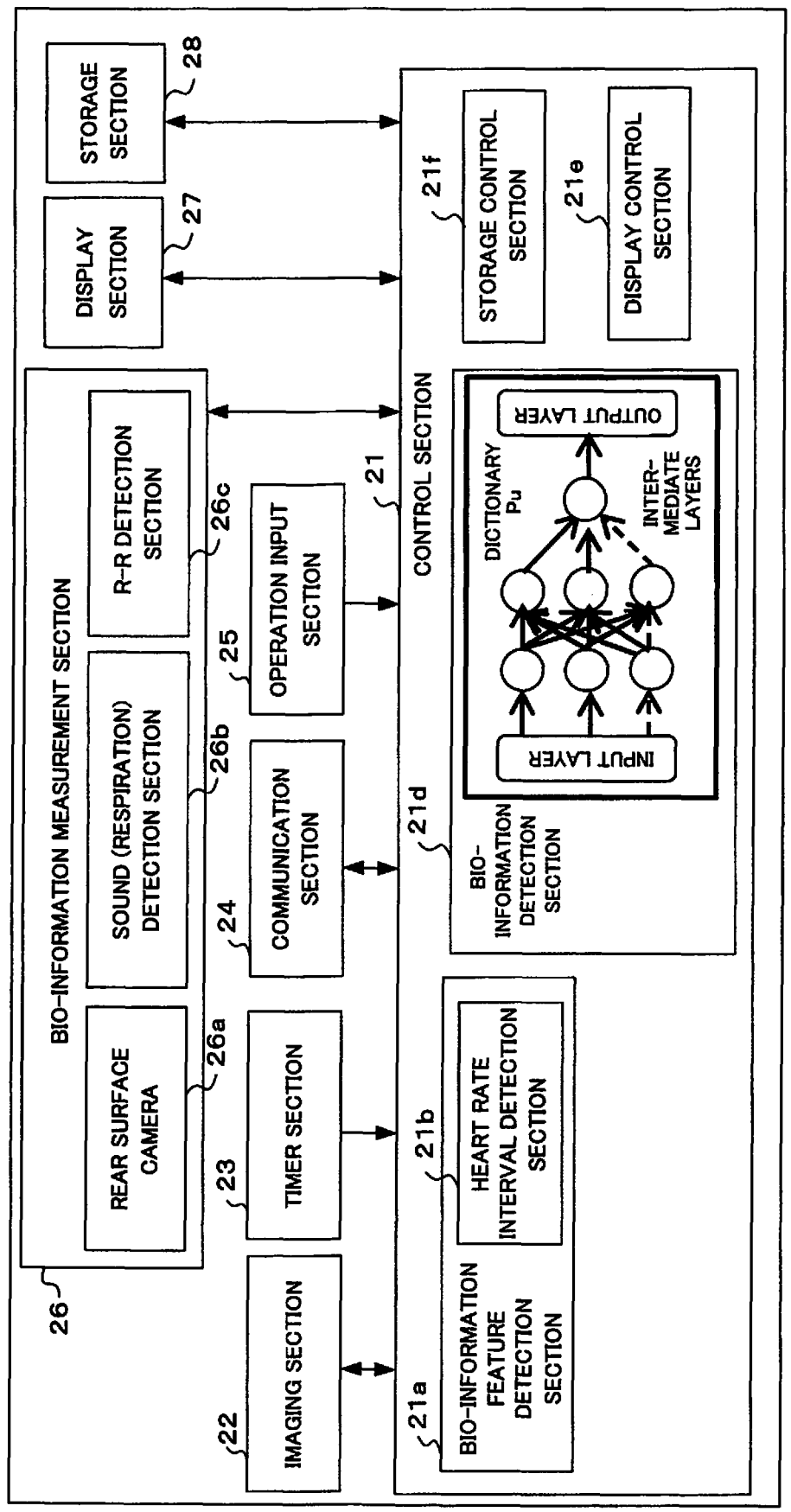
FIG. 2 is a block diagram mainly showing the electrical structure of an imaging terminal of a second embodiment of the present invention.

FIG. 2 is a block diagram mainly showing the electrical structure of an imaging terminal 20 of this embodiment. Description will be given for this embodiment assuming that the imaging terminal 20 is a digital camera. However, the imaging terminal 20 is not limited to a digital camera and may be a portable information terminal such as a smart phone. The imaging terminal 20 comprises a control section 21, an imaging section 22, a clock section 23, a communication section 24, an operation input section 25, a bio-information measurement section 26, a display section 27, and a storage section 28.

The imaging section 22 has a lens for subject image formation, an image sensor, imaging control circuit, imaging signal processing circuit, A/D conversion circuit, etc., converts a subject image to a photoelectric signal, and outputs image data. The clock section 23 has a calendar function and a clock function, and outputs date and time information. The imaging section 22 functions as an image sensor (imaging section) that forms an image of the subject.

The communication section 24 has a communication circuit that performs wired communication or wireless communication with an external unit (including an external server etc.). The operation input section 25 is a user interface for the user to input instructions to be performed to the imaging terminal 20. The operation input section 25 has operation members such as a power switch, release button, mode setting button/dial, cross shaped button, OK button, touch panel etc., and operating states of these operation members are output to the control section 21. The operation input section 25 functions as a shooting operation interface that operates to form an image of a subject.

Figure 6A:
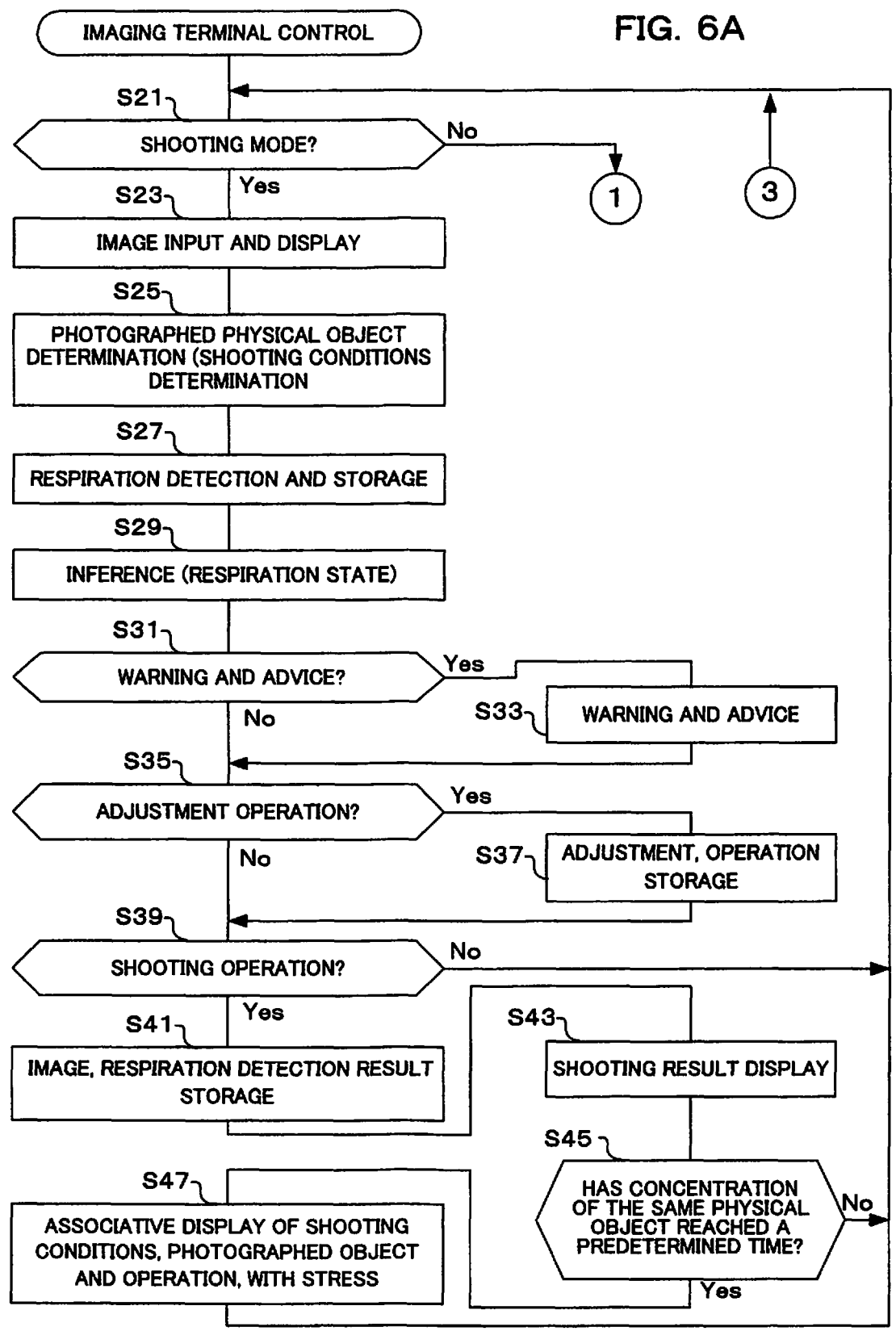

The bio-information measurement section 26 is a processor, and detects bio-information of the user in accordance with instructions from the control section 21 (refer, for example, to S27 in FIG. 6A, and to FIG. 11 and FIG. 12 etc.). With this embodiment, the user's heart rate and respiration are detected as bio-information. As bio-information, besides heart rate and respiration, physiological responses such as pulse waves, peripheral skin temperature, respiration, skin electrical activity, eye movement, brain waves etc. may also be detected. The bio-information measurement section 26 functions as a bio-information acquisition section that acquires bio-information of the operator. The bio-information measurement section 26 functions as a bio-information acquisition section that acquires bio-information of an operator when, during a shooting awaiting action where an instant for acquiring still images is awaited. The bio-information acquisition section also detects at least one physiological response of heart rate, respiration, pulse waves, peripheral skin temperature, skin electrical activity, eye movement, brain waves. The bio-information measurement section 26 functions as a bio-information acquisition section that acquires bio-information of the operator during shooting actions (refer, for example, to S27 in FIG. 6A). It should be noted that although in FIG. 2 the bio-information measurement section 26 is configured with a processor that is separate to the control section 21, the bio-information measurement section 26 may be constructed integrally with the processor constituting the control section 21.

The bio-information detection section 26 has a rear-facing camera 26a, a voice detection section 26b and an R-R detection section 26c. The rear-facing camera 26a has a rear facing lens provided on a raised surface, that is different to the photographing lens provided on the front of the camera, and a rear image sensor. If a color of a hemoglobin component is detected, based on images that have been acquired by the rear-facing camera 26a, it is possible to detect blood flow. Accordingly the rear-facing camera 26a is arranged at a position where it is possible to acquire images of skin portions of the user.

The voice detection section 26b has a microphone and a voice processing circuit etc. The voice detection section 26b detects respiration sounds by collecting the sounds of the user's respiration. The R-R detection section 26c detects intervals between electrical signals at the time of contraction of the heart. When the heart contracts peaks and valleys arise in an electrical signal, and an R signal is an electrical signal that is generated at the time when a part of the heart called a ventricle contracts quickly, and blood is discharged from the heart. An R-R signal is an interval between peaks of this electrical signal. This may also be substituted by a heart beat interval detection section 21b.

The display section 27 has a monitor screen (display), is provided on a main body outer part of a rear screen surface etc. of the imaging terminal 20, and displays live view images, playback images for taken images, menu screens etc. It should be noted that as the display section there may also be an electronic viewfinder with which the user observes images through an eyepiece. The display section 27 also displays stress etc. of the user that has been determined based on bio-information. The display section 27 functions as a display (display section) that displays imaging results from the imaging section (refer, for example, to S23 in FIG. 6A). Display is performed on this display (display section) in accordance with stress condition that has been determined by the stress determination section (refer, for example to FIG. 3A to FIG. 3C, and FIG. 4). In the event that a stress condition that has been determined by the stress determination section is better than a predetermined value, that fact is displayed on the display (display section) (refer, for example, to S5 and S9 in FIG. 1). The display section 27 functions as a display (display section) that displays stress condition.

The storage section 28 is a memory such as electrically rewritable non-volatile memory and stores taken images. Bio-information that has been measured during shooting actions and/or stress information that has been determined based on the bio-information etc. may also be stored in the storage section 28.

The control section 21 is a processor, may be configured using an ASIC (Application Specific Integrated Circuit), and has a CPU (Central Processor Unit), and performs overall control by controlling each section within the imaging terminal 20 in accordance with programs that have been stored in nonvolatile memory. The control section 21 comprises a bio-information feature detection section 21a, a bio-information detection section 21d, a display control section 21e and a storage control section 21f. Each of these sections may be implemented using hardware circuits within the processor, and/or software etc. using programs. The control section 21 and/or the bio-information measurement section 26 function as a processor having a bio-information acquisition section and a stress determination section. This processor also functions as a specified condition detection section.

The control section 21 instructs measurement of bio-information by the bio-information measurement section 26 at a specified time during shooting actions. A time for obtaining bio-information (information representing stress condition) from the bio-information detection section 21d is also determined (refer, for example, to S29 in FIG. 6A and to FIG. 11 and FIG. 12). The control section 21 functions as a specified condition detection section that detects a specified condition during shooting actions in order to acquire images using the image sensor (refer, for example, to S29 in FIG. 6A and to FIG. 11 and FIG. 12). The specified condition detection section determines whether or not the operator has been concentrating on the same physical object for longer than a predetermined time, and if the result of determination is that the user has been focusing for longer than the predetermined time performs display for relevancy of shooting environment and stress condition on the display section (refer, for example, to S45 and S47 in FIG. 6A).

The control section 21 functions as a shooting environment detection section that detects shooting environment, including at least one of shooting conditions, photographed object, and shooting operation (refer, for example, to S25 and S47 FIG. 6A). The control section 21 functions as a shooting environment detection section that detects shooting environment The bio-information feature detection section 21a is input with data that has been detected by the bio-information measurement section 26, and detects features of bio-information. As features of bio-information, with this embodiment, a heart beat interval is detected using the heart beat interval detection section 21b. If it is not possible to determine down to a fine waveform, the heartbeat interval detection section may be substituted with the R-R detection section 26c. Heart beat interval is detected when heart sends blood to the whole body. As features of bio-information, besides this, features of physiological responses such as pulse waves, peripheral skin temperature, respiration, skin electrical activity, eye movement, brain waves etc. may also be detected.

The bio-information detection section 21d is improved with features of bio-information that have been detected by the bio-information feature detection section 21a, and detects the presence or absence of stress and extent of stress etc. With this embodiment, the bio-information detection section 21d has an inference engine and a memory that stores inference models used by the inference engine. This bio-information detection section 21d infers the users stress etc. using inference models that have been generated by deep learning. Generation of inference models will be described later using FIG. 5A and FIG. 5B. It should be noted that besides using an inference engine, whether or not there is stress and extent of stress may also be detected based on features of the bio-information that have been detected by the bio-information feature detection section 21a.

The bio-information detection section 21d functions as a stress determination section that determines stress conditions that shooting actions place on an operator, based on bio-information that has been acquired by the bio-information acquisition section (refer, for example, to S29 in FIG. 6A). The stress determination section determines a first stress condition of the operator in a shooting preparation state during shooting actions, and further determines a second stress condition of the user when imaging results have been displayed after completion of shooting, and in the event that the second stress condition is an improvement over the first stress condition, displays the improvement in stress condition on the display (refer, for example, to S5 and S9 in FIG. 1, and S29 and S47 in FIG. 6A). The bio-information detection section 21 functions as a stress determination section that determines stress conditions that shooting actions place on an operator, based on bio-information that has been acquired by the bio-information acquisition section, when a specified state has been detected by the specified condition detection section (refer, for example, to S29 in FIG. 6A).

The display control section 21e performs control when a through image that has been acquired by the imaging section 22, taken images that have been stored in the storage section 28, stress that has been detected by the bio-information detection section 21d, etc., are displayed on the display section 27.

The storage control section 21f performs storage control when taken images are stored in the storage section 28. Control of storage of bio-information that has been measured during shooting actions and/or stress information that has been determined based on the bio-information etc. in the storage section 28 may also be performed. The storage control section 21f functions as a memory control section that stores stress conditions and shooting environment in association with each other in memory (refer, for example to S41 and S47 in FIG. 6A).

Next, a method of displaying a user's stress, in a case of shooting using the imaging terminal 20, will be described using FIG. 3 to FIG. 3C, and FIG. 4. FIG. 3A shows appearance of a user 31 photographing a wild bird 33 using the imaging terminal 20. In this case the user adjusts the direction in which the camera is facing and focal length so as achieve their intended composition, and performs exposure setting and focusing so as to achieve appropriate exposure (refer to S23 to S29 in FIG. 6A, which will be described later). It should be noted that some of these operations may be performed automatically (using AE and AF for example). While this is happening, the bio-information measurement section 26 acquires bio-information of the user (for example, respiration, heart rate etc.) at specified timing, and stores this information.

FIG. 3B shows appearance of the user 31 having taken the picture and looking at a taken image that has been displayed on the display section 27 (refer to S39 to S47 in FIG. 6A). While this is happening also, the bio-information measurement section 26 acquires bio-information of the user (for example, respiration, heart rate etc.) at specified timing, and stores this information. FIG. 3C shows appearance, after shooting, of display of stress information of the user 31 based on bio-information that has been stored up to now. With this example stress is determined using respiration, and the fact that there is appropriate stress is displayed on the display section 27.

Figure 4:
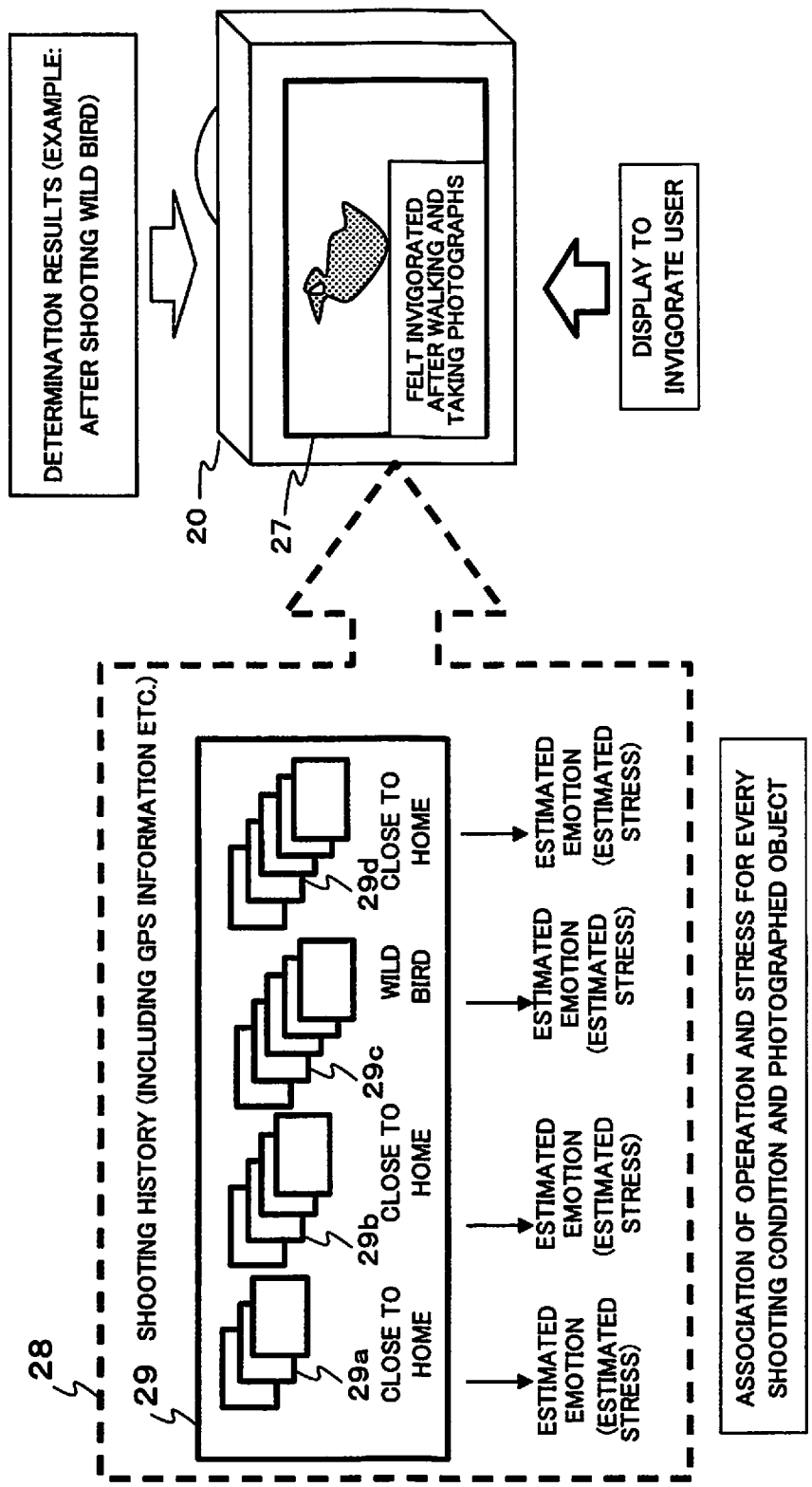
FIG. 4 is drawing describing a usage method for the imaging terminal of the second embodiment of the present invention.

FIG. 4 shows another example of display of stress information (health information). A shooting history 29 that has been stored in the storage section 28 is shown on the left side of FIG. 4. Image groups 29a, 29b, 29d within the shooting history 29 are images that were taken close to home, and are images that were taken in respectively different periods. Also, image group 29c is images that were taken of wild birds. Emotion (stress) is estimated by the bio-information detection section 21d for these respective image groups 29a to 29d, and estimation results are stored in the storage section 28. GPS information representing movement of the user is also stored in the shooting history 29.

These shooting histories 29 are stored in the storage section 28 of the imaging terminal 20. After the shooting of the wild bird 33 shown in FIG. 3A and FIG. 3B, determination of stress etc. is performed and determination results are displayed. With the example shown in FIG. 4, since the result of stress determination has become good, display of "you were invigorated by walking and taking pictures" is performed on the display section 27 so as to invigorate the user. Specifically, if it is determined based on GPS information and each of the image groups 29a to 29d that the user has taken a lot of photographs, and that there was an improvement in good stress each time shooting was performed, this type of display is performed. If this type of displays performed the user will be encouraged to go out and take pictures, and there will be motivation to improve health.

Next, generation of an inference model used in the bio-information detection section 21d will be described using FIG. 5A and FIG. 5B. An inference model is generated using so-called deep learning. First, deep learning will be described. "Deep Learning" involves making processes of "machine learning" using a neural network into a multilayer structure. This can be exemplified by a "feedforward neural network" that performs determination by feeding information forward. The simplest example of a feedforward neural network should have three layers, namely an input layer constituted by neurons numbering N1, an intermediate later constituted by neurons numbering N2 provided as a parameter, and an output layer constituted by neurons numbering N3 corresponding to a number of classes to be determined. Each of the neurons of the input layer and intermediate layer, and of the intermediate layer and the output layer, are respectively connected with a connection weight, and the intermediate layer and the output layer can easily form a logic gate by having a bias value added.

While a neural network may have three layers, if simple determination is performed, by increasing the number of intermediate layer it becomes possible to also learn ways of combining a plurality of feature weights in processes of machine learning. In recent years, neural networks of from 9 layers to 15 layers have become practical from the perspective of time taken for learning, determination accuracy, and energy consumption. Also, processing called "convolution" is performed to reduce image feature amount, and it is possible to utilize a "convolution type neural network" that operates with minimal processing and has strong pattern recognition. It is also possible to utilize a "recursive neural network" (fully connected recurrent neural network) that handles more complicated information, and with which information flows bidirectionally in response to information analysis that changes implication depending on order and sequence.

In order to realize these techniques, it is possible to use conventional general purpose computational processing circuits, such as a CPU or FPGA (Field Programmable Gate Array). However, this is not limiting, and since a lot of processing of a neural network is matrix multiplication, it is also possible to use a processor called a GPU (Graphic Processing Unit) or a Tensor Processing Unit (TPU) that are specific to matrix calculations. In recent years a "neural network processing unit (NPU) for this type of artificial intelligence (AI) dedicated hardware has been designed to be capable being integratedly incorporated together with other circuits such as a CPU, and there are also cases where such a neural network processing unit constitutes a part of processing circuits.

Besides this, as methods for machine learning there are, for example, methods called support vector machines, and support vector regression. Learning here is also to calculate identification circuit weights, filter coefficients, and offsets, and besides this, is also a method that uses logistic regression processing. In a case where something is determined in a machine, it is necessary for a human being to teach the machine how determination is made. With this embodiment, a method of deriving determination of an image by using machine learning is adopted, and besides this may also use a rule-based method that accommodates rules that a human being has experimentally and heuristically acquired.

In FIG. 5A, an inference model 39 is generated in network design 37. Specifically, network design 37 corresponds to the previously described neural network, with data for learning being provided to inputs and outputs of this network design 37, strength of each neuron connection being set, and an inference model generated. Input data 35a and output data 35b for learning are respectively paired. When input data 35a has been input to an input 36, strength of each neuron connection is learned such that output data that is paired with this input data is output from an output 38.

With this embodiment, input data 35a is respiration interval. This respiration interval varies over time, that is, it is variable, as shown in the graph on the left side of FIG. 5A. Also, output data 35b is emotional state corresponding to respiration interval (stress information). Deep learning is performed using many learning data, strength of each neural connection of the network design is determined, and an inference model 39 is generated. With the learning, learning also includes shooting subjects (for example, shooting of wild birds etc.) after the user has walked and repeated shooting.

Also, besides respiration interval, an inference model used in the bio-information detection section 21d may also be generated from heart rate, for example. Heart rate (blood pressure variation) is related to autonomous nerve function, the same as respiration, and can be used to detect stress (emotional state) (refer to non-patent publication 3 described previously). In this case, as shown in FIG. 5B, an inference model may be generated with R-R interval for heart rate as input data 35a, and stress (emotional state) corresponding to this R-R interval as output data 35b.

The inference model that was generated as shown in FIG. 5A is stored in memory of the bio-information detection section 21d. At the time of inference of bio-information (stress etc.), the inference model 39 that was stored in memory is set in an inference engine, and inference is performed using this inference engine.

Figure 6C:
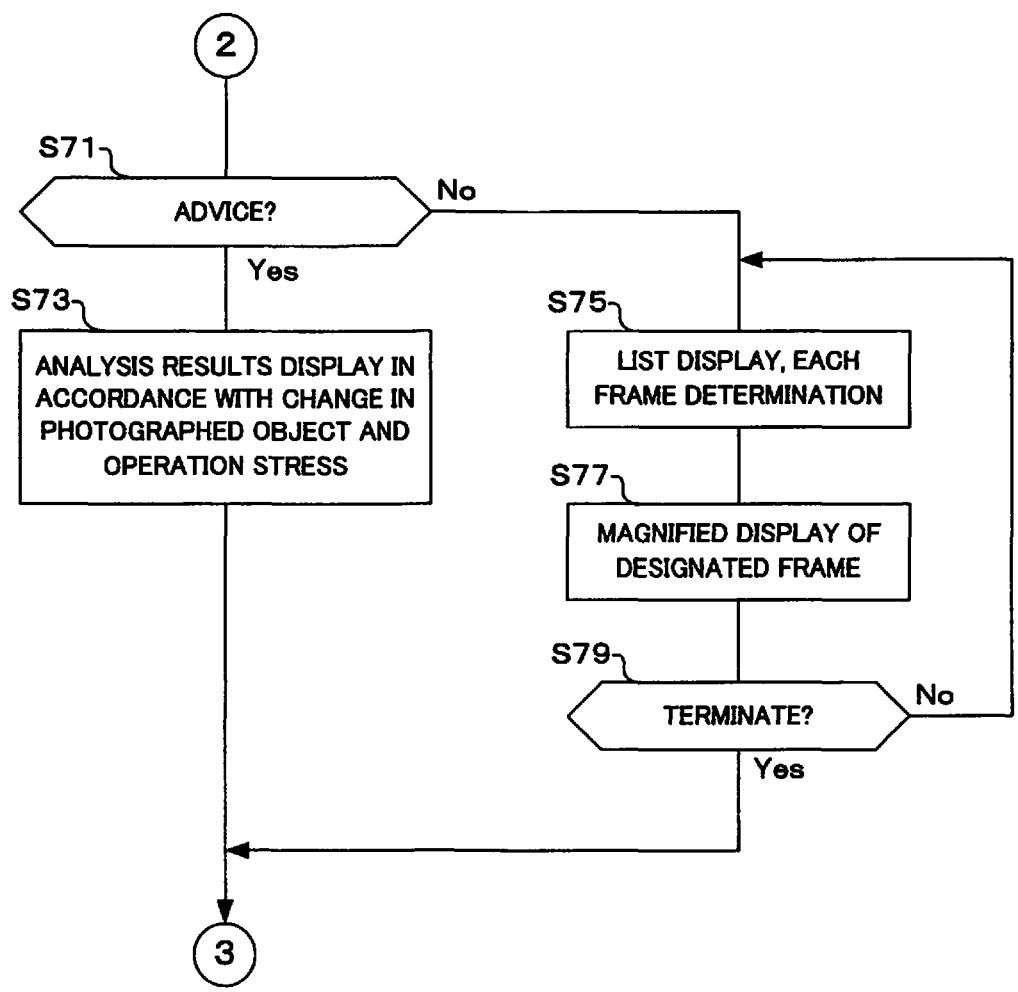

Next, operation of the imaging terminal 20 as an image acquisition device will be described using the flowcharts shown in FIG. 6A to FIG. 6C. This processing flow is executed by the CPU within the control section 21 controlling each section within the imaging terminal 20 in accordance with programs stored in memory.

If the flow for imaging terminal control shown in FIG. 6A and FIG. 6B is commenced, it is first determined whether or not it is shooting mode (S21). The imaging terminal 20 of this embodiment has shooting mode, inference model acquisition mode, advice mode and playback mode, but may have modes other than these modes. Shooting mode is the default mode, and other modes can be set by the user operating the operation input section 25.

If the result of determination in step S21 was shooting mode, an image is input and a through image is displayed (S23). Here, the imaging section 22 inputs image data of a subject image, and after having been subjected to image processing for through image display by the control section 21 a through image (also called a live view image) is displayed on the display section 27.

Next, determination of photographed physical object is performed (S25). Here, an image that has been input is analyzed by the control section 21, and it is determined what a photographed physical object (subject) is (for example, a wild bird, a person etc.). Also, at the time of determination, determination of shooting conditions, such as shooting location, shooting date and time, movement distance until shooting etc. is also performed. These items of information are stored in the storage section 28 or in memory within the control section 21, and may be used at the time of inference of stress etc.

Once a photographed physical object has been determined, respiration detection and storage are performed (S27). Here, the bio-information measurement section 26 detects respiration of the user. Specifically, the voice detection section 26b gathers sound at the time of the user's respiration, and based on this sound detects respiration interval and respiration rate etc., and stores this information in the storage section 28 or memory within the control section 21 etc. It should be noted that as bio-information, other information such as heart rate may also be detected, not only respiration, and further it is also possible to detect blinking of the user's eyes, camera shake when the user is holding the imaging terminal 20 etc. Camera shake can be simply detected if a camera shake sensor is provided in the imaging terminal 20. Further, there is no limitation to the bio-information measurement section 26 within the imaging terminal 20 and bio-information may also be acquired from, for example, a watch (smartwatch), or a terminal having an information acquisition function, such as spectacles.

Next, stress is inferred from respiration state (S29). Here, the inference engine of the bio-information detection section 21d infers state such as stress of the user using the inference model 39 (refer to FIG. 5A), by inputting respiration state that was detected in step S27 to the input layer. It should be noted that inference may also be performed using heart rate, eye blinking, and camera shake etc. as bio-information, without being limited to respiration state. In this case, the inference model 39 is replaced with an inference model that is suitable for the respective bio-information.

Once inference has been performed, it is determined whether or not there is a warning or advice (S31). Here it is determined whether or not the imaging terminal 20 is suitable for performing shooting. For this reason inference may be performed with an inference engine that uses an inference model. For example, there may be cases where a subject composition is not suitable, or exposure is inappropriate etc. Also, if there is excessive stress, since camera shake arises, adjustment of composition and exposure is disordered, a main subject is overlooked, and shutter opportunities are rushed and missed, advice may be performed, such to take deep breaths. There may also be attempts such as determining decision timing from this signal. If there is use of something like a lifelog, it can be used in analysis of the causes of stress etc.

If the of result of determination in step S31 is that there is a warning or advice, the warning or advice is executed (S33). Here, warning of the fact that shooting is not adequate is displayed on the display section 27. Advice etc. so as to make shooting adequate may also be displayed. As advice there are, for example, changing composition by changing shooting direction of the imaging terminal 20, or changing composition by changing focal length, and changing exposure values to achieve appropriate exposure etc. These warnings and advice may be considered when evaluating stress in step S47. It should be noted that if the result of inference is that stress is excessive, warning display may also be performed. In this case exercise may be suggested, and conversely without some stress warning display of the fact that there is a lack of concentration may be performed. A user may be made to relax by conveying the fact that there is appropriate stress by display as in FIG. 3C.

If a warning or advice has been issued in step S33, or if the result of determination in step S31 is that there is no warning or advice, it is next determined whether or not to perform an adjustment operation (S35). As adjustments there are, for example, focusing by the user operating a range ring of the imaging terminal 20 or changing focal length by operating a zoom ring, or setting appropriate exposure by changing exposure values etc.

If the result of determination in step S35 is to perform an adjustment operation, adjustment is executed, and that operation is stored (S37). Here, an adjustment operation that was performed by the user is stored in the storage section 28 or in memory within the control section 21. This adjustment operation may be referenced when evaluating stress in step S47.

If an adjustment operation is stored in step S37 it is next determined whether or not there is a shooting operation (S39). If the user determines shooting composition, a shooting instruction operation (for example, operation of the release button, touch operation of a shooting icon on the display section etc.) is performed at the optimum shooting timing. In this step, it is determined whether or not this operation has been performed. If the result of this determination is that a shooting operation has not been performed, processing returns to step S21.

On the other hand, if the result of determination in step S39 is that a shooting operation has been performed, image data is stored, and a respiration detection result is stored (S41). Here, image data is acquired from the imaging section 22 at the time when the shooting operation was performed, and after applying image processing for storage to this image data the image data is stored in the storage section 28. Also, respiration information that was detected at the time of the shooting operation or immediately before the shooting operation is stored in the storage section 28 in association with image data.

Once images and respiration detection results have been stored, next, shooting results are displayed (S43). Here, images that are the same as those stored in the storage section 28 are displayed on the display section 27. Using this display it is possible for the user to confirm taken images. During this confirmation, bio-information is measured, the same as in step S7 of FIG. 1, and display is performed based on measurement results. As this display, stress ST1 that was measured during shooting actions and stress ST2 that was measured during playback display of taken images are compared, and if stress has improved that fact may be displayed. Also, if stress ST2 that was measured during playback display of taken images has improved, this fact may also be displayed.

Once shooting results have been displayed, it is next determined whether or not a time for which the same physical object has been concentrated on exceeds a predetermined time (S45). Here, determination may be based on measurement results from the bio-information measurement section 26. Determination may also be based on image analysis as to whether or not image data that has been acquired is for the same physical object. Determination may also be based on whether shooting has been performed by the user at the same location, based on GPS information etc. By performing focusing on framing etc. concentrating on the same physical object, it can be said that the brain has been activated. It should be noted that the predetermined time only has to be a time to an extent that it is deemed the same physical object has been concentrated on. If the result of this determination is that the time for which the same physical object has been concentrated on is less than the predetermined time, processing returns to step S21.

If the result of determination in step S45 is that the same physical object has been concentrated on for longer than the predetermined time, shooting conditions, photographed object and operation, and relevancy of stress are displayed (S47). As shooting conditions there are various conditions such as in what environment and in what season was the user walking, was shooting performed indoors or outdoors etc., in what time frame was shooting performed, such as in the morning, during the day, at nighttime etc., and under what weather conditions was shooting performed, such as in cloudy conditions, rain etc. As photographed objects they are, for example, people, pets, flowers, scenery, buildings, wild birds etc., and these can be detected by analyzing image data. Also, as operations there are the warning of step S33, and the adjustment operations of step S37. There are also focus operations of the imaging terminal 20, operations to change focal length, exposure adjustment operations etc.

In step S47, association between these items of information and stress that has been detected by the bio-information detection section 21d is obtained, and these associations are displayed on the display section 27. For example, messages such as "walking and shooting, became invigorated" or stress was reduced as a result of being satisfied with taken images even if there were factors that cause stress". Also, in addition to display, the storage control section 21f may store stress conditions and shooting environment in association with each other in the storage section 28 or memory within the control section 21. Once association display has been carried out, processing returns to step S21.

Returning to step S21, if the result of this determination is not shooting mode, it is next determined whether or not to acquire an inference model (S51). With this embodiment, the bio-information detection section 21d performs inference of stress etc. using an inference model. This inference model will be a different inference model depending on input data and output data. An inference model that corresponds to the user's intentions is therefore generated in the bio-information detection section 21d. Acquisition of this inference model is set in the operation input section 25. A plurality of inference models may also be prepared, in accordance with use. It should be noted that when generating an inference model a large amount of learning data is used and computation is also massive, and so a request may be issued to an external learning device.

If the result of determination in step S51 is to acquire an inference model, first, age and gender are designated (S53). Stress etc. is significantly affected by age and gender of the user who is using the imaging terminal 20, and so when requesting generation of inference model these items of information are set.

Next, training data is created (S55). Here, as was described in FIG. 5A pairs of data representing stress etc. for bio-information are generated, these data are made training data (data for learning). If previous bio-information and stress at that time are stored in pairs within the imaging terminal 20, these items of information can be used as training data. It should be noted that an external learning device may gather data that has been stored in another server, and this data may be made training data.

Next, an inference model is generated (S57). Here, an inference model is generated using training data that was created by the bio-information detection section 21*d* in step S55.

Once an inference model has been generated, it is next determined whether or not reliability of respiration interval and emotion (state) is greater than a predetermined value (S59). Here, a LOSS value is obtained. Specifically, inference is performed using a correct solution that was not used at the time of generating the inference model, and for which bio-information (respiration interval) and output data (stress (emotion information)) are known, and reliability of the inference model is determined. Once reliability has been obtained, it is determined whether or not this reliability is greater than a predetermined value.

If the result of determination in step S59 is that reliability is low, a learning matrix is reset (S63). Here, since reliability of the inference model is low, a learning matrix used in inference is changed. If the learning matrix has been changed, processing returns to step S57, and generation of an inference model is performed again.

On the other hand, if the result of determination in step S59 is that reliability is greater than the predetermined value, the inference model is stored in the imaging terminal (S61). Here, the inference model that was generated in step S57 is stored. It should be noted that a plurality of inference models may also be stored for each application, and applications may be associated with inference models when they are stored. Once the inference model has been stored processing returns to step S21.

Returning to step S51, if the result of this determination is not to acquire an inference model, it is next determined whether or not there is advice display (S71). When the user takes pictures, there may be cases where they want advice in order to take a photograph that is like what they want. In this type of case, advice display is set in the operation input section 25. Advice display may be set with this type of manual setting, and may be automatically displayed as required.

If the result of determination in step S71 is that there is advice display, analysis results are displayed in accordance with photographed object and operating stress change (S73). Here, results of having determined at what time, from discovery of a physical object, adjustment of composition and parameters, up to shooting, there was emotional movement, that was determined as stress etc., are displayed. For example, analysis is performed at the time of determining composition, at the time focus is achieved, or at a time such as at the instant of shooting (may be estimated based on bio-information before and after shooting). From this analysis it proves that a state of unconscious concentration contributes to peace of mind etc., and it is possible to know what type of physical objects and shooting techniques are suitable for one's own health. It is also possible to ascertain differences etc. for each shooting, and it is also possible to understand stress at the time of using devices and accessories. These data are accumulated and transmitted to the maker and a service station, and it is possible to perform improvements to products and usability, and to service etc., based on this data.

Also, in step S73, advice display may also be performed using an inference engine within the bio-information detection section 21*d*. For example, in a case where stress has become significant, that fact may be displayed, and conversely in a case where photos that satisfy the user are ascertained, and stress has been lowered, this fact may also be displayed. It should be noted that content of the advice display may be transmitted to a portable terminal etc., and it may be possible to display advice on the portable terminal etc. Once advice display has been performed, processing returns to step S21.

On the other hand, if the result of determination in step S71 is that there is not advice display, list display and respective frame determination are performed (S75). Here, as processing for a case where it has been determined that there is no advice display, an example of playback mode is shown. In order to perform playback display this display is performed using thumbnail images on the display section 27, based on image data that is stored in the storage section 28. It is also determined whether or not the user has designated a particular frame from within the list display.

Next, a designated frame is subjected to magnified display (S77). If a particular frame has been designated by the user with the operation input section 25 in step S75, image data for this designated frame is read out from the storage section 28, and magnified and displayed on the display section 27. Here, stress conditions at the time of shooting may also be displayed. If the user is made aware that photographs that have been taken in stressed situations actually appear to be enjoyable, then the next time similar shooting will be preferably performed and techniques for shooting in that field are improved. Further it is possible that there will be the desire to go and actively perform that type of photography. This type of camera could also be in a product category that could be called health cameras. It should be noted that here emotions to be displayed etc. may also be performed with organism detection, and naturally, manual input is also possible.

It is next determined whether or not there is completion (S79). If the user has completed playback mode, a completion operation for the playback operation is performed using the operation input section 25. If the result of determination in step S79 is not completion, step S75 is returned to, and playback mode continues. On the other hand, in the case of completion the playback mode is terminated, and step S21 is returned to.

In this way, with the second embodiment of the present invention, bio-information is measured during shooting actions (S27), and together with storage of this bio-information, bio-information such as respiration state is inferred based on the measurement result (S29). Then, if shooting is performed, bio-information (result of inference) such as respiration state is stored together with storage of images (S41). This means that it is possible to collect bio-information of the user during shooting actions, and to evaluate stress after that based on this information.

Also, with the second embodiment of the present invention, if the user concentrates on the same physical object for longer than a predetermined time (this state is called a "specified state"), association of shooting conditions etc. and stress is displayed (S45, S47). Specifically, in a case where focusing on framing etc. have been performed by concentrating on the same subject, there may be cases where the brain is activated. In this type of case, shooting conditions (for example how many steps were taken etc.), photographed object (for example, wild bird etc.), and operating conditions (for example zooming was performed, framing was performed by changing direction of the photographing lens etc.) are displayed in association with the effects they had on stress. For example, if display of "Although there was a lot of walking, after looking at the taken images there were photographs that were satisfactory, and so stress was lowered" etc. is performed, it is possible to encourage the user.

Also, with the second embodiment of the present invention, stress is inferred using an inference model. Knowing stress from respiration state is not simply a relationship between the two, but it is possible to simply estimate stress by using an inference model.

Next, a third embodiment will be described using FIG. 7A to FIG. 10C. With the second embodiment only the imaging terminal 20 was standalone, but with this embodiment the imaging terminal 20 operates in cooperation with an external management server 10. The management server 10 has medical checkup information of the user, and stress information of the user can be displayed in association with the medical checkup information. It should be noted that the management server 10 may access medical checkup information that is stored in another external server, and acquire this medical checkup information. According to this embodiment routine behavior is associated with medical examinations and diagnostic records under quiet conditions when in hospital, precision of a user's health determination and health care guidelines is increased, health care guidance etc. is received in real time for routine behavior, and it becomes possible to support a healthier life.

Figure 7A:
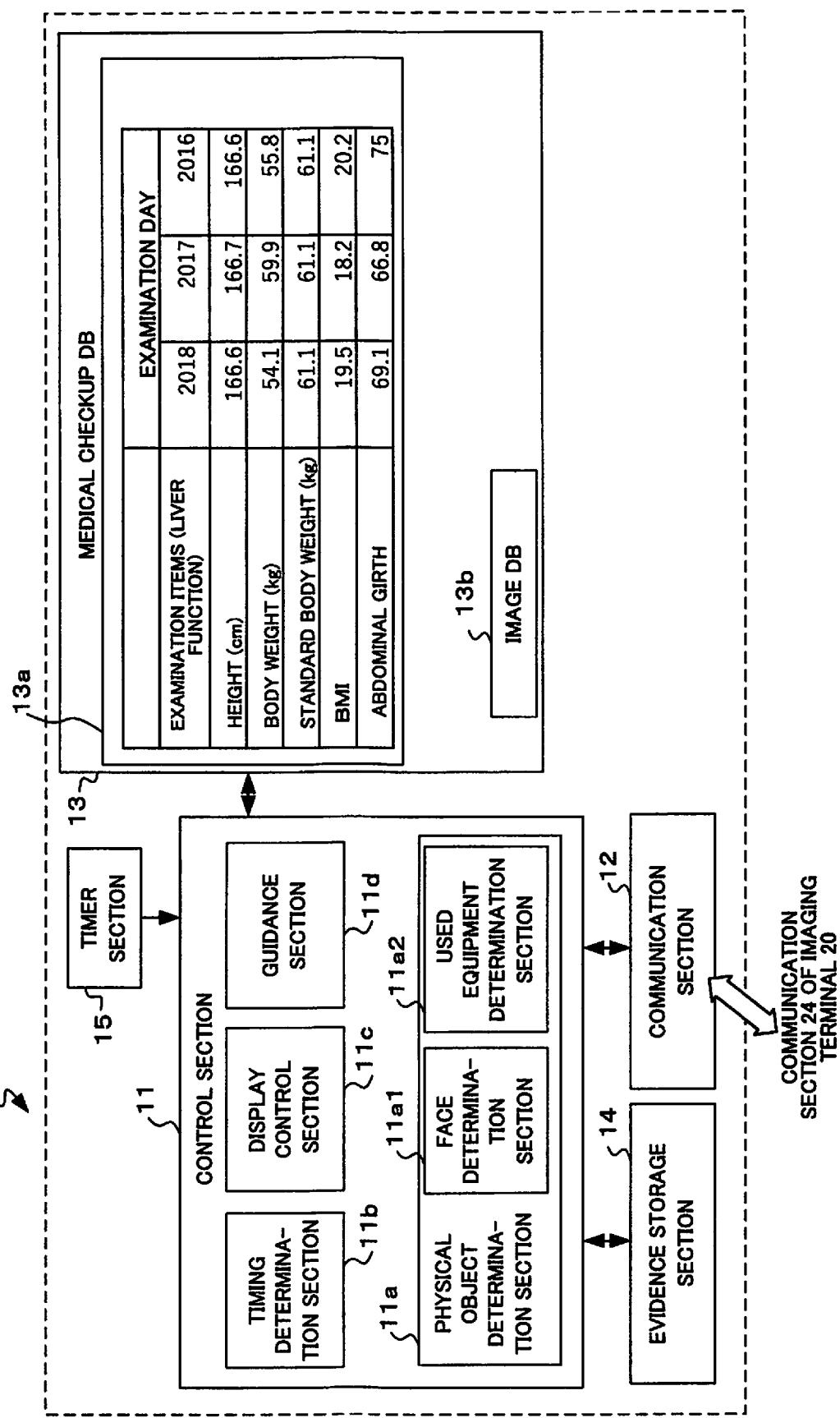
FIG. 7A is a block diagram mainly showing the electrical structure of a management server within an imaging system of a third embodiment of the present invention.
Figure 7B:
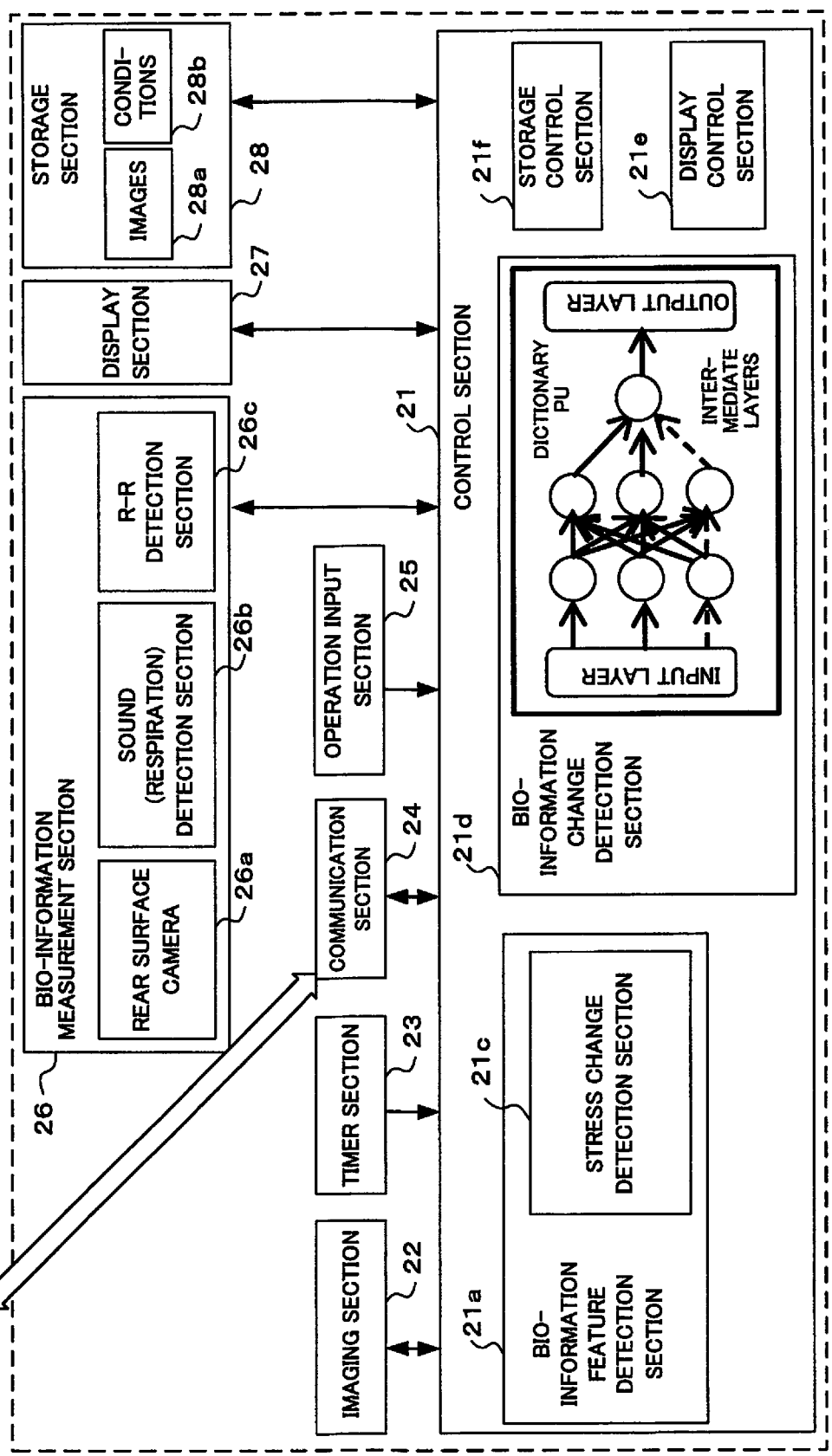
FIG. 7B is a block diagram mainly showing the electrical structure of an imaging terminal within the imaging system of the third embodiment of the present invention.

FIG. 7A is a block diagram mainly showing the electrical structure of the management server 10, and FIG. 7B is a block diagram mainly showing the electrical structure of the imaging terminal 20. Both communication sections 12 and 24 are capable of connecting to the Internet etc. by wired communication or wireless communication, and it is possible to communicate data and commands by means of the Internet. With this embodiment, as will be described later, the management server 10 is a server that is installed inside the hospital, and the imaging terminal 20 is a portable information terminal, and has a function as a patient terminal.

The management server 10 functions as a system server, and comprises a control section 11, communication section 12, database 13 evidence storage section 14 and clock section 15. The management server 10 functions as a server that is provided externally to the imaging terminal that has an image sensor. The server has a database and an advice creation section. The server transmits advice that has been created by the advice creation section to the imaging terminal, and this imaging terminal displays the advice on a display (refer, for example, to FIG. 8 and S111 in FIG. 10A).

The communication section 12 has a communication circuit that is capable of performing transmission and reception to the communication section 24 of the imaging terminal 20, and it is possible to connect to the communication section 24 by means of the Internet etc. The communication section 12 functions as a communication circuit for performing communication with the portable information terminal.

The database (DB) 13 has a medical checkup DB13a and an image DB13b. The medical checkup DB13a holds at least health check results of the user of the imaging terminal 20. In a case where the medical checkup DB13a is not provided within the management server 10, health check results are obtained by accessing a database in which health check results of the user of the imaging terminal 20 are stored, by means of the communication section 12. The image DB13b stores image data of third parties, without being limited to users of the imaging terminal 20. The database 13 functions as a database that stores health check results of the operator. The database 13 functions as a database that stores health check results of the operator of the portable information terminal.

The evidence storage section 14 is a memory, and stores health check results of the user that have been retrieved from the medical checkup DB13a in response to a request from the imaging terminal 20 and transmitted from the imaging terminal 20, and information that has been transmitted from the imaging terminal 20, as evidence. In this case, transmission time and date and reception time and date are stored in association with identification data of the imaging terminal 20. As a result of this storage, relationships between a state of resting in a hospital, such as a medical checkup, and information during activity, such as shooting actions, are regulated. Based on the storage, what type of activity is linked with what type of diagnosis, and what types of health promotion measure there are becomes useful information at the time of creating guide information in the guidance section 11d. The clock section 15 has a calendar function and a clock function, and outputs date and time information.

The control section 11 is a processor, may be configured using an ASIC (Application Specific Integrated Circuit), and has a CPU (Central Processor Unit), and performs overall control by controlling each section within the imaging terminal 20 in accordance with programs that have been stored in nonvolatile memory. The control section 11 comprises a physical object determination section 11a, a timing determination section 11b, a display control section 11c, and a guidance section 11d. Each of these sections may be implemented using hardware circuits within the processor, and/or software etc. using programs.

The control section 11, the control section 21 and/or the bio-information measurement section 26 function as a processor having a bio-information acquisition section and a stress determination section. The processor determines stress factors based on bio-information but has been acquired by the bio-information acquisition section and relevancy of health check results that have been stored in the database (medical checkup DB 13), and has an advice creation section that creates advice based on the stress factors (refer to the guidance section 11d, FIG. 8, and S111 in FIG. 10A). The processor (1) receives bio-information of the operator from the portable information terminal by means of the communication circuit (refer, for example, to S47a in FIG. 9, and S103 in FIG. 10A) (2) determines stress factors based on the bio-information that has been received and relevancy of health check results that have been stored in the database (refer, for example, to S111 in FIG. 10A), and (3) creates advice based on the stress factors (refer, for example, to S111 in FIG. 10A). The server 10 transmits advice that has been created by the processor to the portable information terminal, and displays advice on a display of this portable information terminal (refer, for example, to FIG. 8).

The physical object determination section 11a determines physical objects within an image that has been transmitted from the imaging terminal 20. There is an abundance of information included in images that have been acquired at the time of shooting, and the physical object determination section 11a outputs advice to the guidance section 11d by making effective use of this information. For example, it is possible to determine things the user cannot notice by themselves, such as whether the user is relaxed when photographing flowers, or excited when photographing birds. Also, a specific example to be given as advice can be considered what kind of photograph shooting is recommended depending on the health condition. In determining routine actions of the user, with this embodiment description has been given of examples of an imaging apparatus and a camera, but since there is a possibility of there being domestic appliances and equipment other than these, it is made possible to acquire equipment information (including domestic appliance information). Information on accessories may also be acquired.

It is possible to expect that similar effects will be obtained by determining a relationship between shooting actions and health with a camera even by using information such as that a particular television program appears to be good for health, or health conditions appear to be stable when listening to particular music on audio equipment, etc. Also, when it comes to a camera as an example for an application, information such as health condition was good when on a trip with particular person is useful, and information on "face" is important in analyzing who that person was, and it therefore becomes possible to narrow down such as to "with family" and "with friends". Although not specified here, applied scenes and operation detection results of that shooting terminal may also be subjected to a determination by the physical object determination section 11a, and with the example of television or audio, performing detection of content becomes important.

The physical object determination section 11a has a face determination section 11a1 and an applied equipment determination section 11a2. The face determination section 11a1 detects faces within images. If features of the face of a user are registered in advance, determination can be performed easily. If the features of the face of a user are not registered, it is determined that a person is a physical object.

Taking a camera as an example, then as was described previously, the applied equipment determination section 11a2 determines unit type of the imaging terminal 20, and determines a device that is being used in the imaging terminal 20, for example, a telephoto lens having a focal length of x mm. If the applied equipment is known, it is useful in determining a physical object. For example, with a telephoto lens there is a possibility of determining that a physical object is a wild bird. With a macro lens, a determination that shooting is being performed for flowers etc. can also be helpful information, and it is possible to determine favorite equipment from information as to whether a lens is telephoto, or wide angle, or macro, and determine that that equipment is effective for health, which facilitates more specific advice.

In the event that determination of stress etc. is performed in the control section 11, the timing determination section 11b determines timing for the determination. Change in a person's bio-information is dependent on the activity or action at that time, and so it is preferable to unitarily manage timing on the management server. It also becomes possible to create evidence taking into consideration whether the person is in a hospital, or being treated, and further if they are sleeping, eating, or taking medicine etc. Further, cooking time, time spent in the bath, time spent drinking tea etc. may also be determined using information on other domestic appliances. For example, even if there is stress during shooting, overall determination, such as relieving stress with a break when returning home, also becomes possible. Also, since relevancy of actions of the user can be easily found on the internet or a network, shopping information, cost information, information on routes taken etc. may also be associated with card procedures etc.

Also, the management server 10 receives accesses from not only the imaging terminal 20, but also from various terminals such as a doctor terminal or terminal within a hospital etc. For this reason, the timing determination section 11b may also perform control of timing etc. of responses to various terminals. It should be noted that details of the determination timing will be described later using FIG. 11 and FIG. 12.

Figure 8:
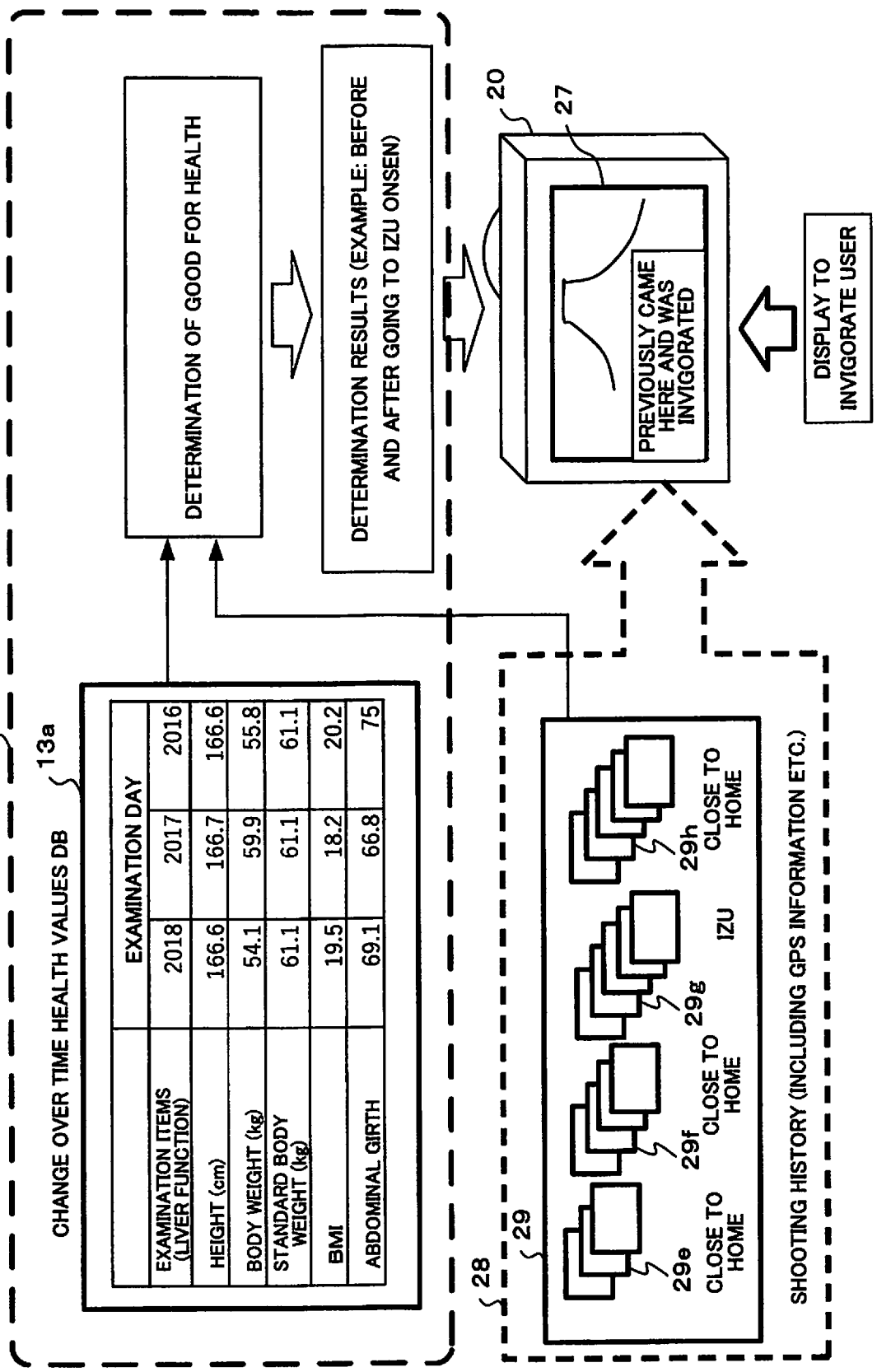
FIG. 8 is a drawing describing linking of health check results and bio-information that has been acquired at the time of shooting, in the imaging system of the third embodiment of the present invention.

The display control section 11c performs control of display in the case of receiving image data in the imaging terminal 20 by means of the communication section 12 The guidance section 11d performs guidance display together with performing display on the imaging terminal 20, based on the medical checkup DB13a (refer, for example, to FIG. 8). At this time the guidance section 11d may also associate, for example, stress and health check results. The guidance section 14 functions as an advice creation section that determines stress factors based on bio-information that has been acquired by the bio-information acquisition section and relevancy of health check results that have been stored in the database, and that creates advice based on these stress factors (refer, for example, S111 in FIG. 10A).

The imaging terminal 20 is configured similarly to the imaging terminal 20 that was shown in FIG. 2. The same reference numerals are attached to the same blocks (sections), and detailed description is omitted. The communication section 24 functions as a communication circuit and can perform transmission and reception of data and commands to and from the management server 10 etc. using wired communication or wireless communication. A through image etc. is displayed on the display section 27, and determination results for stress condition are displayed. The display section 27 also displays determination results for stress condition in association with health check results (refer to FIG. 8). The display section 27 functions as a display (display section) that displays images in which stress condition that has been determined by the stress determination section, and medical checkup information of the operator are associated with each other (refer, for example, to the display section 27 in FIG. 8).

The storage section 28 is an electrically rewritable non-volatile memory, and has a storage region for storing images 28a and conditions 28b. The images 28a that are stored are taken images. Also, the conditions 28b that are stored are conditions such as shooting conditions during shooting actions, for example, how far has been walked, shooting time and time frame (for example, evening) when shooting was performed. Also, similarly to the storage section 28 of FIG. 2, besides these items of information, Bio-information that has been measured during shooting actions and/or stress information that has been determined based on the bio-information etc. may also be stored in the storage section 28.

There is a stress change detection section 21c within the bio-information feature detection section 21a. The stress change detection section 21c detects change in stress conditions of the user based on changing respiration that has been detected by the voice detection section 26b, and change in heart rate that has been detected by the rear-facing camera 26a and the R-R detection section. It should be noted that in the event that the bio-information measurement section 26 can detect bio-information other than respiration and heart rate, stress change may also be detected based on these other items of information.

Also, stress change may also be detected in cooperation with the management server 10, by receiving determination results of the management server 10 or determination results from a doctor etc. by means of communication. While heart rate is acceptable as bio-information, change may be detected by acquiring bio-information other than heart rate.

For example, there may be cooperation with a smart phone or wearable terminal that is possessed by the camera user, and brain waves, blood flow, body temperature, and other bio-information may also be used. An adapter having dedicated sensors may be attached to the camera, and it made possible to perform sensing of bio-information. It is also possible to perform determination by gathering necessary data without an adapter, but communicating with the wearable terminal.

Next, display of the third embodiment of the present invention will be described based on change in stress conditions, using FIG. 8. The medical checkup DB13a is stored in the DB13 of the management server 10. Change over time for respective detection items is stored in this medical checkup DB13a. With the example shown in FIG. 8, if body weight is considered, for example, weight gradually reduces, and in connection with this weight loss abdominal girth and BMI are also lowered.

Shooting histories 29 are stored in the storage section 28 within the imaging terminal 20. Images groups 29e, 29f and 29h within the shooting history 29 are images that were taken close to the user's (photographer's) home, and these image groups are of things that were photographed in different periods. Also, the image group 29g is images that were taken when the user took a trip to Izu. Emotion (stress) at the time of shooting is estimated by the bio-information detection section 21d for these respective image groups 29e to 29h, and estimation results are stored in the storage section 28 as shooting history 29. GPS information representing movement of the user is also stored in the shooting history 29.

The shooting history 29 is transmitted from the imaging terminal 20 to the control section 11 of the management server 10 via the communication sections 24 and 12. The guidance section 11d within the control section 11 determines what has been good for health based on the medical checkup DB13a stored in the DB13 and the shooting history that has been received from the imaging terminal 20. With the example shown in FIG. 8 the control section 11 analyzes, from the medical check up DB13a, that reduction in body weight results in improvement in numerical values relating to health, and looks for causes of those improvements from the shooting history 29. As a result, it is determined that health was good before and after going to the hot springs of Izu. The imaging terminal 20 receives this determination, and performs text display of "you were invigorated when you came here before", and selects and displays an image from the image group 29g that was created in Izu before, on the display section 27. By looking at this display the user will feel good, and will look forward to going and taking photographs. As was described previously, determinations need not only be made through photography, and it is also possible to determine what is good for health by estimating actions before and after shooting in cooperation with other devices, and by specifying details of actions, such as is did the person smoke after shooting, or was a photograph taken of Mount Fuji at the time of having boarded the Shinkansen.

Figure 9:
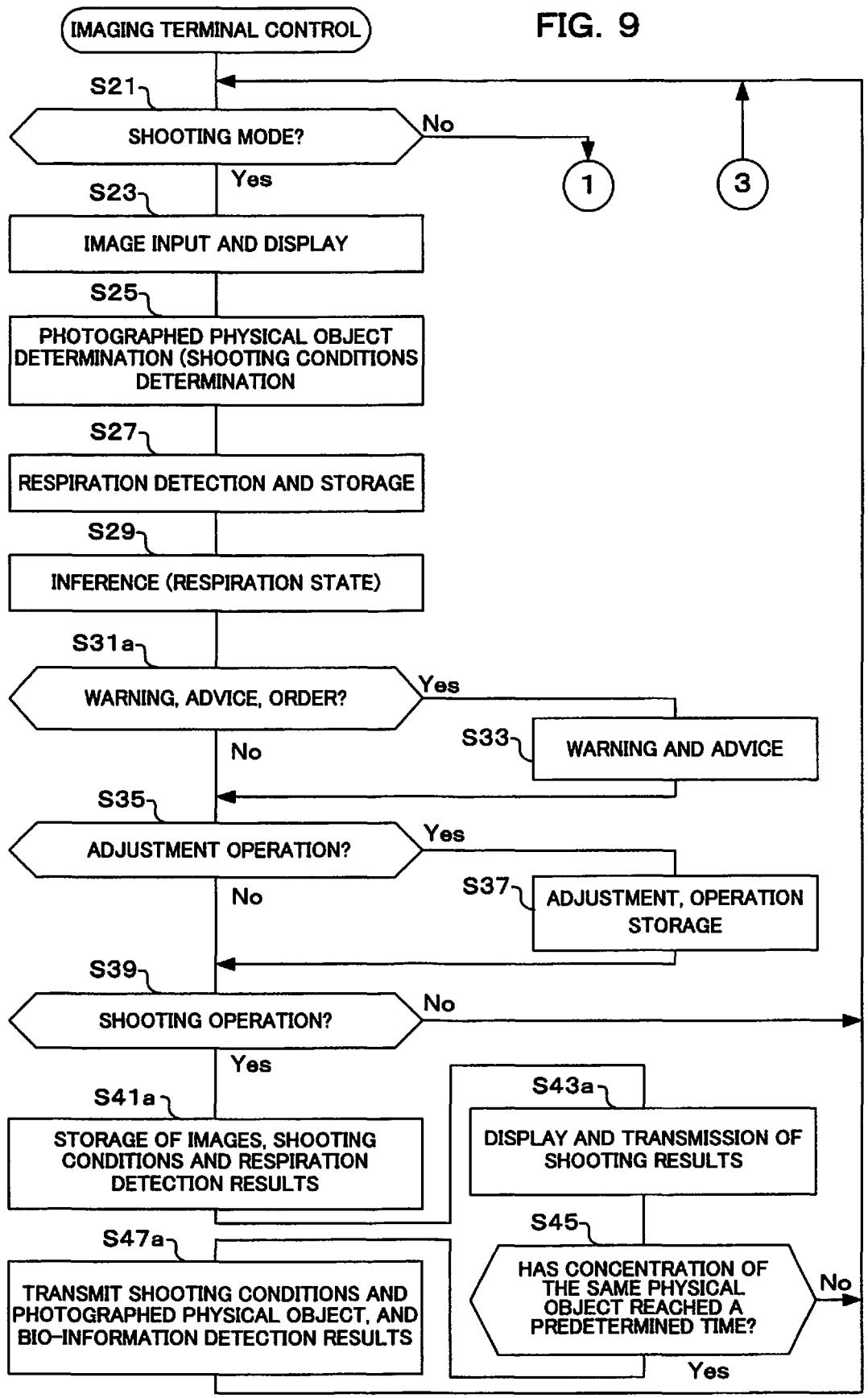
FIG. 9 is a flowchart showing operation of an imaging terminal within the imaging system of the third embodiment of the present invention.
Figure 10A:
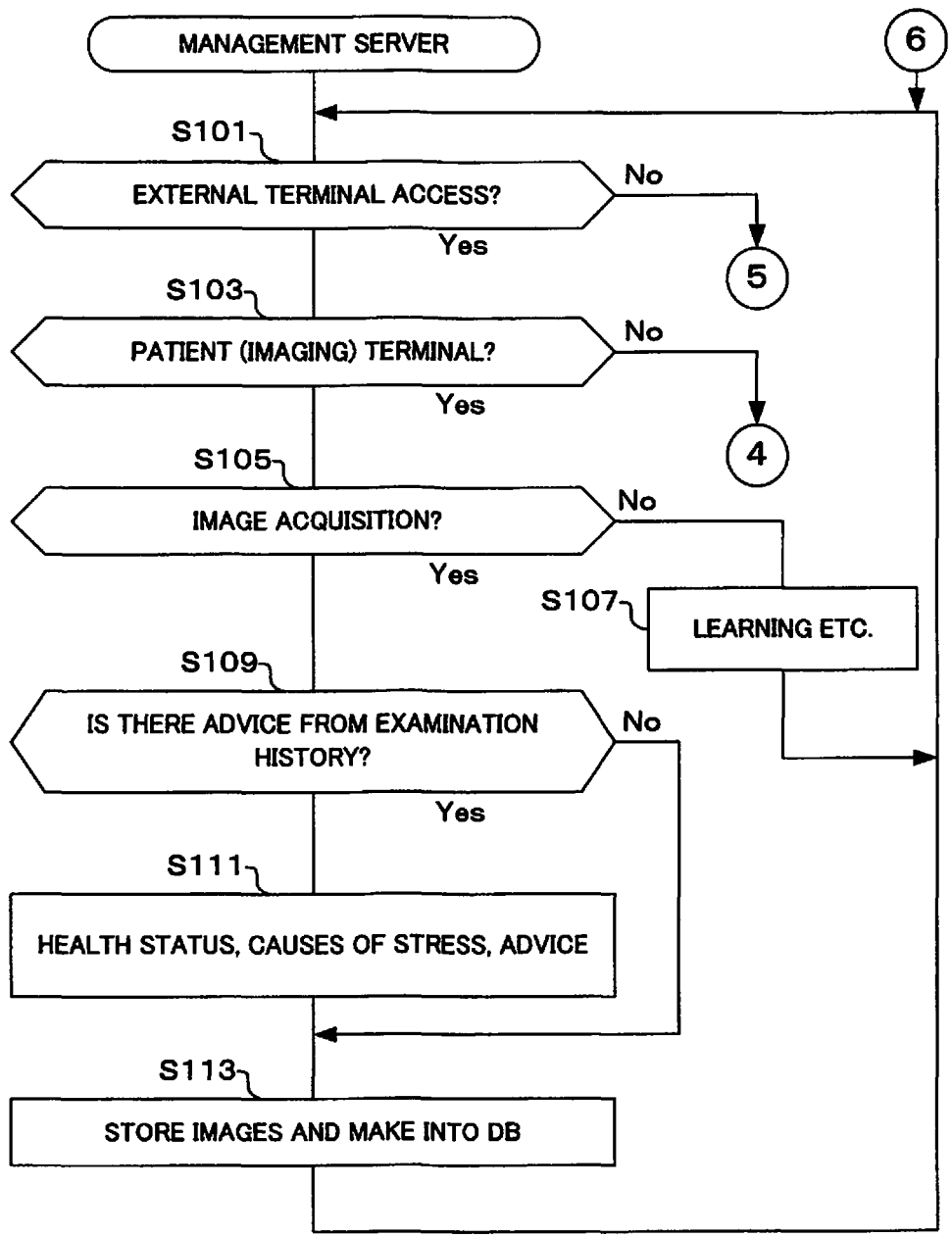
FIG. 10A to FIG. 10C are flowcharts showing operation of a management server within the imaging system of the third embodiment of the present invention.
Figure 10B:
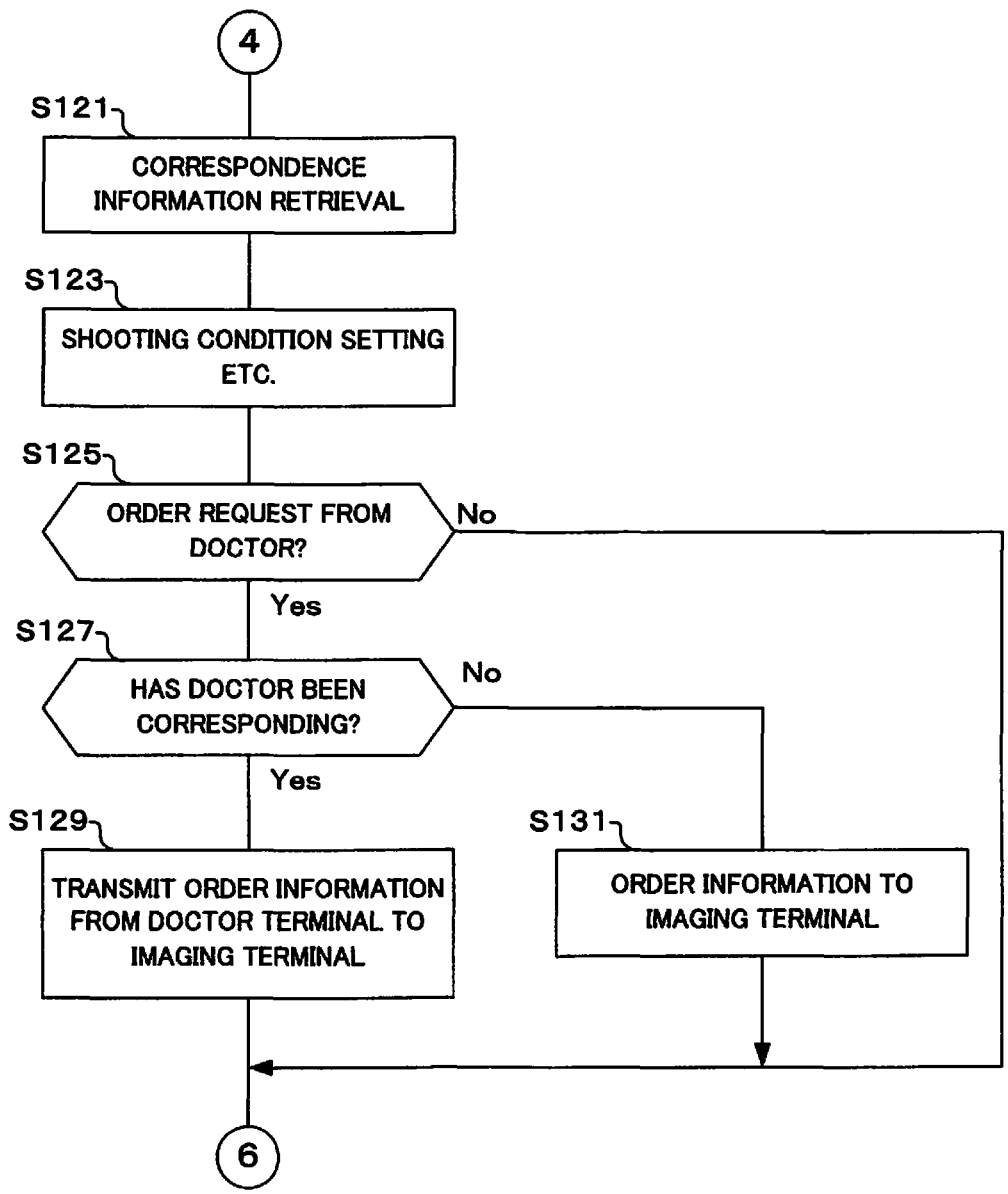
Figure 10C:
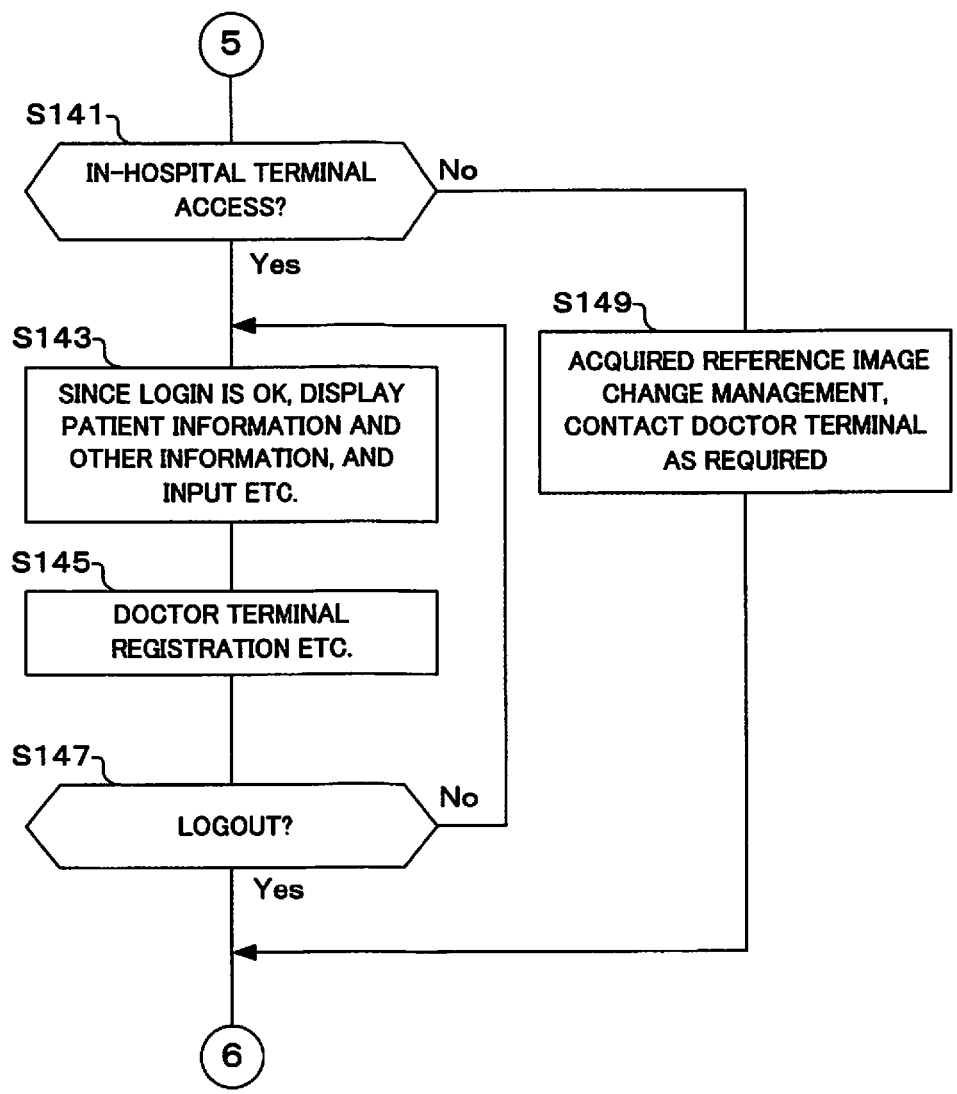

Next, operation of the third embodiment will be described using the flowcharts shown in FIG. 9 to FIG. 10C. FIG. 9 shows operation of the imaging terminal 20, as a patient terminal. This processing flow is executed by the CPU within the control section 21 controlling each section within the imaging terminal 20 in accordance with programs stored in memory. It should be noted that the flowchart shown in FIG. 9 is substantially the same as the flowchart that was shown in FIG. 6A, and description will center on points of difference.

If the flow for imaging terminal control is commenced, it is first determined whether or not it is shooting mode (S21). Similarly to the case of FIG. 6A, with this embodiment also, shooting mode is the default mode. If the result of this determination is that it is not shooting mode, playback mode or communication mode is executed. Detailed description of processing for these modes is omitted.

If the result of determination in step S21 is shooting mode, image is input and through image display is performed (S23). Then, determination of physical object and shooting conditions is performed (S25), respiration is detected, detection results are stored (S27), and inference of respiration state is performed (S29). Once inference has been performed, it is next determined whether there is a warning, advice, or an order (S31a). Warnings and advice are the same as for the case of previously described FIG. 6. An order is a case of order information being transmitted, in step S129 or S131, which will be described later. In this step it is determined whether or not order information has been received.

In a case where an order is to perform shooting using a specific request, shooting can be performed in line with that order, and it is possible to reflect the intentions of the person who issued that order. For example, as was described in this application, there may be cases where it is easier to ascertain health condition by specifically looking at face color or visually observing change in an affected area than by detecting bio-information from heart rate etc. In this case it becomes possible for this shooting terminal to further contribute towards health management of a user if it is made possible to receive orders from a doctor, such as taking and transmitting a picture of a face with this camera, or taking and transmitting a photograph of a diseased part for observations.

If the result of determination in step S31a is YES, warning or advice are issued (S33). Here, in addition to the processing for the case of FIG. 6, in the event that order information has been received this order is displayed.

If a warning or advice have been issued in step S33, or if the result of determination in step S31a is No, it is next determined whether or not there is an adjustment operation (S35). If the result of this determination is Yes, adjustment and operation storage are performed (S37). Here, the user performs adjustment for the imaging terminal 20. As adjustment there are, for example, the user changing composition by changing shooting direction of the imaging terminal 20, or changing composition by changing focal length, and changing exposure values to achieve appropriate exposure etc. Once adjustment has been performed, adjustment operations that were performed by the user are stored in the storage section 28 etc.

Once adjustment has been performed in step S37a, or if the result of determination in step S35 is No, it is next determined whether or not a shooting operation is been performed (S39), and if a shooting operation has not been performed processing returns to step S21. On the other hand if a shooting operation has been performed an image and shooting conditions are stored (S41a). Shooting conditions are, for example, how far was walked, in what place was shooting performed, what time period was shooting performed etc. Also, respiration detection results at the time of shooting are stored.

If storage of images and shooting conditions etc. has been performed, next shooting results are displayed, and shooting results are transmitted (S43a). Here, taken images are displayed on the display section 27, and bio-information of the user at this time is measured and stored. This is in order to detect stress condition etc. Also, shooting results etc. are transmitted to the management server 10.

Next, it is determined whether or not the same physical object has been concentrated on for a predetermined time (S45). It is determined whether or not the user has been concentrating on the same physical object. If the result of this determination is that the time the user has been concentrating for is less than the predetermined time, processing returns to step S21. On the other hand, if the concentration time is greater than the predetermined time, shooting conditions and physical object information, and bio-information detection results, are transmitted (S47a). Here, shooting conditions, photographed physical object, and bio-information detection results that have been respectably acquired are transmitted to the management server 10. The management server 10 creates advice display based on these items of information. If advise display has been received from the management server, advice display is performed on the display section 27 (refer, for example, to the display section 27 in FIG. 8). Once the processing of step S47a has been executed, processing returns to step S21.

It should be noted that step S45 is omitted from the flowchart shown in FIG. 9, and if a shooting operation has been performed regardless of the time for which the same physical object has been concentrated on, images, shooting conditions and respiration detection results are stored, and after having displayed shooting results on the display section the information that is stored may be transmitted to the management server. In this case various analysis and determination such as was the same physical object photographed, with what frequency were operations performed, are performed by the management server. The photographing terminal may also share some of those operations and information.

Next, operation of the management server 10 will be described using the flowcharts shown in FIG. 10A to FIG. 10C. This processing flow is executed by the CPU provided in the control section 11 controlling each section within the management server 10 in accordance with programs stored in memory. As was described previously, with this embodiment the management server 10 is arranged inside the hospital, and is capable of being connected to a terminal other than the imaging terminal 20, such as a doctor terminal that is used by doctor, or a personal computer etc. that is connected to an intranet within the hospital, as a patient.

If the flow for the management server is commenced, it is first determined whether or not there is an access from an external terminal (S101). The management server 10 is capable of connecting to various external terminals as well as to the imaging terminal 20. Also, as was described previously, with this embodiment the management server 10 is a server that is arranged within a hospital. This means that there will also be access from in-hospital terminals (refer to S141 in FIG. 10C). In this step S101 it is determined whether or not there has been access to the server from the imaging terminal 20, or another external terminal, such as a doctor terminal.

If the result of determination in step S101 is that there has been access from an external terminal, it is next determined whether or not there is access from a patient terminal (imaging terminal) (S103). Here it is determined whether or not there has been access from the imaging terminal 20 that was shown in FIG. 7B. With this embodiment the management server 10 is handled as an in-hospital server, so that it is also possible to consider health status as a cause of stress by associating the bio-information and medical checkup DB13a. Also, a patient terminal means a terminal or group of terminals that are carried by a patient. In recent years there has been an increase in people performing activities while carrying smart phones or wearable information terminals, and although these devices constitute patient terminals on their own or in cooperation, an imaging terminal may be utilized in determining health state of user at the time of shooting. However, there are sufficient functions for advice other than shooting and bio-information acquisition in some imaging terminals, and those functions may be shared in other information terminals.

If the result of determination in step S103 is that there is a patient terminal (imaging terminal), it is next determined whether or not there is image acquisition (S105). Images that have been taken by the imaging terminal 20 are transmitted from the communication section 22 to the management server 10 (refer to S47a in FIG. 9). In this step determination is based on whether or not images have been transmitted from the imaging terminal.

If the result of determination in step S105 is not image acquisition, learning etc. is performed (S107). The imaging terminal 20 issues a request for an inference model for inference that will be performed in the bio-information detection section 21d, to the outside. Here, determination is based on whether there has been a generation request for this inference model. If learning etc. has been performed, processing returns to step S101.

On the other hand, if the result of determination in step S105 is image acquisition, it is next determined whether or not there is advice from the health history (S109). The health examination DB 13a is stored in the DB13 of the management server 10, and in this health examination DB13a health values (for example, body weight etc.) are stored in such a manner that change over time can be recognized. Also, in step S47a shooting conditions, photographed physical object information and bio-information is received from the imaging terminal 20, and history of these items of information is stored. It is then determined, based on information from the imaging terminal 20 and change in health values that have been stored in the medical checkup DB13a, whether there is advice to the user who is using the imaging terminal 20. This advice may be input by a doctor in advance, and may be created by inference, using an inference model that has been generated by deep learning.

If the result of determination in step S109 is that there is advice, advice is created based on health conditions and stress factors (S111). Here, in a case where it can be said, from health values, that health condition is bad, causes of degradation in health are search for using inference etc. based on stress information that has been stored in the imaging terminal 20. Similarly, in a case where, from health values, health status has become good also, causes of improvement in health are searched for using inference etc. based on stress information that has been stored in the imaging terminal 20. In this case, as well as inference results for improvement in health, results of the evidence storage section 14 may also be displayed. In particular, there is also a need, not only with medical examinations and diagnoses, for the user themselves to perform a confirmation check on relationships between actions and results of medical checkups.

If advice has been created in step S111, or if the result of determination in step S109 is that there is no advice, images are stored and made into a database (S113). Here, images that were acquired in step S105 are stored in the image DB13b of the DB 13. Also, in the case where advice has been created in step S111, this advice is also stored. As a result of this storing, in a case where there is access from the imaging terminal 20 this advice is transmitted and can be displayed (refer to FIG. 8). For example, in a case where it is determined in step S103 that there was an access from the imaging terminal 20, and in step S109 it is determined that there is advice, in steps S111 or S113 advice is transmitted to the imaging terminal 20. The imaging terminal 20 displays advice on the display section 27 if advice has been received.

Returning to step S103, if the result of this determination is that there is not a patient terminal (imaging terminal), retrieval of corresponding information is performed (S121). In the event that there is not a patient terminal (imaging terminal), a doctor terminal access is issued. For example, in a place where there is a doctor etc. there will be requests from patients and warnings from the system (refer to S149), and if the need arises to confirm health condition of a specified patient, it is necessary to confirm medical history and consultation history of that patient. Therefore, the doctor accesses the management server 10 in the hospital in order to retrieve various information. There may also be cases where a doctor requests retrieval of information relating to users who use the patient terminal (imaging terminal). In this step, therefore, the management server 10 performs retrieval in accordance with these requests.

Next, setting of shooting conditions etc. is performed (S123). There may be cases where additional information about the patient is acquired, and telephone confirmation or mail confirmation of current conditions is performed. In this case it is possible that there will be instructions to the user who is holding the imaging terminal such as to photograph and send current conditions (by mail attachment etc.). Such measurement is described as "setting of shooting condition" in step S123. In this step, there is emphasis on shooting function and there are cases where a request for shooting is issued to the imaging terminal 20, as a patient terminal, via a doctor terminal, and setting of conditions for this shooting etc. is illustrated. For example, in a case where a doctor believes that face color of the user who is been photographed with the imaging terminal is poor, in order to confirm the face complexion, there will be cases where shooting is requested with instruction on shooting condition setting.

If shooting conditions have been set, it is next determined whether or not there is actually an order request from a doctor (S125). For example, if shooting conditions etc. were set in step S123, in this step it is determined whether or not there is an order request for a shooting request. Besides this it is determined whether or not it is a case of a doctor wanting to send a request (order) for medical care, relating to the user (patient) who is using the imaging terminal. Determination may also be regarding whether there is necessary advice from the health check results. If the result of this determination is that there is not an order from a doctor, processing returns to step S101.

If the result of determination in step S125 is that there is an order from the doctor, it is determined whether or not the doctor will contact the patient (S127). Here, determination is for whether or not advice (or information) has been directly transmitted from the doctor terminal to the patient terminal (imaging terminal 20). Transmission of this type of order is not only performed when the user instructs manually, and if it is simply a repeat of a particular order that has already been determined it is not necessary to bother the doctor.

If the result of determination in step S127 is that the doctor corresponds personally, order information is transmitted from the doctor terminal to the imaging terminal by means of manual operation etc. (S129). In this case, it is possible to input a detailed order, that would be impossible to designate, with an order that has been automatically set.

On the other hand, if the result of determination in step S127 is that the doctor will not contact the patient directly, order information is transmitted to the imaging terminal (S131). In this case there is a demand for retrieving only follow-up changes for specified items, and the doctor is not troubled. In step S129 or S131, the management server 10 transmits an order (or advice) which has been created manually by a doctor, or created automatically under the supervision of the doctor, to the imaging terminal 20.

If order information has been transmitted in step S129 or S131, processing returns to step S101. It should be noted that in step S129 or S131, order information is transmitted to the imaging terminal, but this is not limiting and in a case where order information is stored within the management server 10 and there is an access from the imaging terminal, the order information may be transmitted.

Returning to step S101, if the result of determination in this step is that there is not an access from an external terminal, it is determined whether or not there is access from an in-hospital terminal (S141). As was described previously the management server 10 is provided inside the hospital, and in this step it is determined whether or not there was an access from terminal within the hospital.

If the result of determination in step S141 is that there was an access from a terminal in the hospital, it is next determined whether or not login is OK (S143). It is determined whether or not an access from the in-hospital terminal has been performed using a login password etc. so as to prevent illegal access. If login has been performed only information on the patient etc. pertaining to the request, and other information, is displayed on the in-hospital terminal. Also, in a case where there is input information from the in-hospital terminal to the management server 10 input of this information is performed.

Next, registration etc. of the doctor terminal is performed (S145). Here, processing to register the doctor terminal in the management server 10 is executed. Processing to register a patient terminal (imaging terminal) may also be performed. If there is no terminal registration request, this step may be skipped.

It is next determined whether or not there is a logout (S147). When access from the in-hospital terminal to the management server 10 is completed, logout processing is performed. In this step it is determined whether or not this logout processing has been executed. If the result of this determination is that logout processing has not been performed, processing returns to step S143. On the hand, if logout processing has been performed processing returns to step S101.

Returning to step S141, if the result of determination in this step is that there is not an access from an in-hospital terminal, change processing for acquired reference images is performed on a regular basis (S149). This is a step which it is advisable to invoke because appropriate images and stress condition of patients have been successively accumulated, and in a case where there has been some kind of specified change (using programmed detection and inference that uses artificial intelligence) procedures are performed to make this known to the doctor, or make it known to a patient or other family member. Specifically, notifications are transmitted to respective terminals. That is, in previously described step S113 etc. images were acquired and stored. In this step S149, for those images that have been acquired, changes are managed every specified period. For example, for the same patient changes to images are administered. This administering of change may be performed by a doctor, but may also be performed using artificial intelligence that utilizes deep learning. If there is a need for medical care or diagnosis from the image changes, a doctor terminal of the doctor in charge of the patient is contacted. As required, the doctor in charge transmits order information to the patient terminal (refer to S129). Once image change management has been performed, processing returns to step S101.

In this way, with the third embodiment of the present invention, it is possible for the imaging terminal 20 to cooperate with the management server 10. In addition to change in stress conditions that have been detected in the imaging terminal 20, it is possible to display precise advice by considering change over time in medical checkups stored in the management server 10. Specifically, not only is there acquisition of bio-information for comparatively resting states at the time of medical checkup or at the time of medical examination, or under special conditions when in a hospital, bio-information and stress information is also acquired for states of activity in daily life. Then, by comprehensively judging these items of information it is possible to present more highly reliable measures for promotion of health and health maintenance. For example, emergency notification may be issued to a doctor depending on the circumstances, and it becomes possible to perform information gathering necessary for supporting a diagnosis in consideration of daily life information which previously was rarely shared. At the patient side also, it is possible to present whether every specific activity is good or bad for health, including whether or not that activity should be continued. For example, in a situation where there is some kind of problem or anxiety, it is possible to present clear advice to the user of the imaging terminal 20 in real-time (refer to FIG. 8).

Next, determination timing for each embodiment of the present invention be described using FIG. 11. In the timing determination shown in FIG. 11, functions of a determination timing judgment section 41 and a stress judgment section 43 are executed by the control section 21 within the imaging terminal 20. It should be noted that in the third embodiment some of those functions are executed by control section 11 the management server 10.

With the example shown in FIG. 11 camera operation information and camera bio-information are acquired in the imaging terminal 20. Here, the camera operation information is information relating to the release operation and button operation, within the operation input section 25. Also, as camera operation information shooting information at the time of taking photographs with the imaging section 22 is also acquired, for example, focal length of a photographing lens, focus position of the photographing lens, and exposure control values (such as shutter speed, aperture value, ISO sensitivity).

Also, as camera bio-information there are camera shake data and respiration data. The camera shake data is data from a camera shake sensor or the like that is provided in the imaging terminal 20. Also, respiration data is data based on the sounds of respiration of the user that have been detected by the voice detection section 26*b* within the bio-information measurement section 26. It should be noted that the items described in FIG. 11 as bio-information and camera operation information are illustrative examples, and other information may also be added.

For the above-described camera bio-information and camera operation information, each item of data can be acquired at specified time intervals by the determination timing judgment section 41 (control section 21). Specifically, each item of data can be acquired at times t1, t2, . . . .

External bio-information may be acquired by a unit that is external to the imaging terminal 20. For example, a sensor for bio-information acquisition is provided in a unit that the user is equipped with, such as a smart phone, and bio-information is acquired using the sensor. Heart rate data, muscle strength data, perspiration data etc. are acquired as these bio-information. Data is exchanged between the external unit and the imaging terminal 20 at a specified timing using wireless communication etc. With the example of FIG. 11, acquisition of data is performed at times T11, T12, and T13. Since communication consumes electrical power, and electrical power to the external unit is restricted, compared to a case of acquiring bio-information using the internal sensors of the imaging terminal 20, data acquisition interval is wide.

The stress judgment section 43 provided inside the imaging terminal acquires camera bio-information and camera operation information at times T11, T12 and T13, and also requires external bio-information to perform stress judgment. Specifically, the camera bio-information on camera operation information is acquired at narrow (short) time intervals of time t1, t2, . . . , but the external bio-information can be acquired at wide (long) time intervals of times T11, T12 and T13.

Also, the determination timing judgment section 41 may transmit data to the stress judgment section 43 at a predetermined time that is within the time at which the determination timing judgment section 41 acquired the camera bio-information or the camera operation information. As the predetermined time there are, for example, time at which the user has performed operation to press the release button down halfway, time at which the user has performed operation to press the release button down fully, and time at which there has been a change from a moving state to a stationary state based on camera shake data etc. By performing stress judgment at this type of specified time, compared to the case of performing stress judgment constantly it is possible to prevent power wastage. By setting the specified time to a time when there is a break in shooting operations, it is easy to judge the stress condition for a series of shooting actions up to that point, and it is possible to increase reliability of judgment results.

Next, a modified example of the determination timing will be described using FIG. 12. With the example that was shown in FIG. 11, the determination timing judgment section 41 determined determination time for camera operation information and camera bio-information. With this modified example however, the determination timing judgment section 41 only determines determination time for camera operation information. Determination timing for camera bio-information is determined by the stress judgment section 43. Accordingly, the stress judgment section 43 determines determination time for camera bio-information and external bio-information, and stress condition is judged at this time.

In this way, by widening determination times for camera bio-information, such as camera shake data and respiration data, it is possible to prevent power supply wastage for data acquisition. Since camera operation information only detects operating state of the camera, then compared to a case where camera bio-information is acquired wasting of power is slight, and so it is possible to further lower power wastage with this modified example.

As has been described above, with each of the embodiments of the present invention an image of the subject is formed (refer, for example, to S23 in FIG. 6A), a specified state within shooting actions for acquiring the subject image is detected to acquire bio-information of the operator (refer, for example, to S27), and when the specified condition has been detected determination of stress conditions that those shooting actions place on the operator are determined based on bio-information (refer, for example, to S29). Shooting conditions etc. and stress conditions are then displayed in association with each other (refer, for example, to S47). As a result it is possible to detect that actions that contribute to health are being performed without the user being aware. Specifically, stress is associated with health, and it becomes possible to detect that state of health has improved as a result of indulging in photography.

Also, in each of the embodiments of the present invention, an image of the subject is formed (for example S23 in FIG. 6A), bio-information of the operator drawing shooting actions is acquired (refer, for example, to S27), stress conditions that the shooting actions place on the operator are determined based on bio-information (refer, for example, to S29), and stress conditions are displayed (S47). As a result it is possible to make known that actions that contribute to health are being performed without the user being aware. Specifically, since stress information is detected based on bio-information that has been acquired during shooting actions, by confirming this stress condition it is possible for the operator to know that there has been a contribution to health without them being aware. Also, a display system that has been shown in each of the embodiments of the present invention acquires bio-information of an operator during operation actions of equipment that has been provided in advance (refer, for example, to S1 in FIG. 1A, S27 and S41 in FIG. 6A, S27 in FIG. 9, and S12 in FIG. 11), and display is performed on a display in accordance with stress conditions (refer, for example, to S5, S9 and S13 in FIG. 1A, S33 and S47 in FIG. 6A, S73 in FIG. 6(c), and S33 and S47a in FIG. 9). As a result it is possible to display stress information of the operator based on operation actions of equipment.

It should be noted that in each of the embodiments of the present invention, bio-information of a photographer has been acquired for shooting actions using an imaging device. As well as at the time of operating an imaging device, this bio-information can similarly be acquired at the time of operating operation members of a portable information terminal, for example, and it is possible to determine stress condition based on the bio-information at this time. There is also no limitation to a portable information terminal, and bio-information can also be acquired at the time of operating various devices, such as a desktop computer, medical equipment such as an endoscope, optical equipment such as a microscope, industrial devices etc., and it is possible to determine stress conditions based on bio-information at this time. With these units also, there are parts that are touched by the user's hands and feet, or, if there is eyepiece confirmation display etc., the operators head also touches the unit. Therefore, sensors for acquiring bio-information in a contact or non-contact manner are provided on these parts, and acquisition of bio-information becomes easy. Also, when the user is equipped with peripheral units, such as a mouse or keyboard, a head-mounted display or spectacles type terminal, or a microphone for voice input or a watch type terminal, bio-information may be acquired from the peripheral units at the time those units are about to be operated or about to be used.

Also, although the control sections 11 and 21 are constructed as a processor, besides being implemented in the form of the previously described hardware circuits, or software using a CPU and programs, they may be constructed with hardware circuits, or may have a hardware structure such as gate circuitry generated based on a programming language described using Verilog, or may use a hardware structure that uses software, such as a DSP (digital signal processor). Suitable combinations of these approaches may also be used.

Also, with this embodiment, an instrument for taking pictures has been described using a digital camera, but as a camera it is also possible to use a digital single lens reflex camera or a compact digital camera, or a camera for movie use such as a video camera, and further to have a camera that is incorporated into a mobile phone, a smartphone, a portable information terminal, personal computer (PC), tablet type computer, game console etc., a medical camera, or a camera for a scientific instrument such as a microscope, a camera for mounting on a vehicle, a surveillance camera etc. In any event, it is possible to adopt the present invention as long as a device is capable of acquiring bio-information. Since the imaging device has a reference operation of forming an image, detection having referenced that is easy, but this application can also be applied to an information acquisition device that is for other than photography, and to a display device with some operations. Also, in the case of shooting actions, a release operation for shooting etc. may be taken as a basic operation that constitutes a reference, there may be other operations, and there may also be specified reference operations that are set in advance and stored in the database or storage section. If operations are performed often at the time of using these devices, a lot of information is acquired. By being set as specified operations, it is possible for data collected under specified conditions to be subjected to analysis for such conditions.

Also, among the technology that has been described in this specification, with respect to control that has been described mainly using flowcharts, there are many instances where setting is possible using programs, and such programs may be held in a storage medium or storage section. The manner of storing the programs in the storage medium or storage section may be to store at the time of manufacture, or by using a distributed storage medium, or they be downloaded via the Internet.

Also, with the one embodiment of the present invention, operation of this embodiment was described using flowcharts, but procedures and order may be changed, some steps may be omitted, steps may be added, and further the specific processing content within each step may be altered. It is also possible to suitably combine structural elements from different embodiments.

Also, regarding the operation flow in the patent claims, the specification and the drawings, for the sake of convenience description has been given using words representing sequence, such as "first" and "next", but at places where it is not particularly described, this does not mean that implementation must be in this order.

As understood by those having ordinary skill in the art, as used in this application, 'section,' 'unit,' 'component,' 'element,' 'module,' 'device,' 'member,' 'mechanism,' 'apparatus,' 'machine,' or 'system' may be implemented as circuitry, such as integrated circuits, application specific circuits ("ASICs"), field programmable logic arrays ("FPLAs"), etc., and/or software implemented on a processor, such as a microprocessor.

The present invention is not limited to these embodiments, and structural elements may be modified in actual implementation within the scope of the gist of the embodiments. It is also possible form various inventions by suitably combining the plurality structural elements disclosed in the above described embodiments. For example, it is possible to omit some of the structural elements shown in the embodiments. It is also possible to suitably combine structural elements from different embodiments.

What is claimed is:

1. An imaging system, comprising:
a shooting operation interface that operates to form an image of a subject, and
a processor that has a bio-information acquisition section and a stress determination section, wherein
the bio-information acquisition section acquires bio-information of an operator when, during shooting awaiting action where an instant for acquiring still image is awaited, the shooting operation interface is operated, and
the stress determination section determines stress conditions that shooting actions place on the operator based on the bio-information that has been acquired using the bio-information acquisition section.

2. The imaging system of claim 1, further comprising:
a display that displays imaging results from an image sensor, and wherein
the display performs display of the stress conditions that have been determined by the stress determination section.

3. The imaging system of claim 1, wherein:
a display displays images in which stress condition that has been determined by the stress determination section and medical checkup information of the operator has been associated.

4. The imaging system of claim 1, wherein the processor further comprises:
a shooting environment detection section that detects shooting environment that includes at least one of shooting condition, photographed object and shooting operation; and
a memory control section that stores the stress conditions and the shooting environment in memory in association with each other.

5. The imaging system of claim 1, further comprising:
a display that displays imaging results from an image sensor, and wherein
the processor, in a case where stress condition that has been determined by the stress determination section is better than a predetermined value, displays that fact on the display.

6. The imaging system of claim 1, further comprising:
a display that displays imaging results from an image sensor, and wherein
the stress determination section determines a first stress condition of the operator in a shooting preparation state during shooting actions, and further determines a second stress condition of the operator when imaging results have been displayed on the display after completion of shooting using the image sensor, and in the event that the second stress condition is an improvement over the first stress condition, displays the improvement in stress condition on the display.

7. The imaging system of claim 1, wherein:
the bio-information acquisition section detects at least one physiological response of heart rate, respiration, pulse waves, peripheral skin temperature, skin electrical activity, eye movement, and brain waves.

8. The imaging system of claim 1, further comprising:
a display that displays imaging results from an image sensor; and
a sensor that detects shooting environment, wherein
the processor has a specified condition detection section that detects a specified condition, during shooting actions for acquiring images using the image sensor, wherein
the specified condition detection section determines whether or not the operator has been concentrating on the same physical object for longer than a predetermined time, and if the result of determination is longer than the predetermined time displays association of the shooting environment and the stress conditions on the display.

9. The imaging system of claim 1, wherein the processor further comprises:
a specified condition detection section that detects a specified condition, among shooting actions for acquiring images using an image sensor, and wherein the stress determination section, when a specified condition has been detected by the specified condition detection section, determines stress conditions that the shooting actions place on the operator based on the bio-information that has been acquired using the bio-information acquisition section.

10. The imaging system of claim 1, further comprising:
a database that stores health check results of the operator, wherein
the processor determines stress factors based on bio-information that has been acquired by the bio-information acquisition section, and relevancy of health check results that have been stored in the database, and has an advice creation section that creates advice based on these stress factors.

11. The imaging system of claim 10, wherein:
there is a server that is external to the imaging terminal that has an image sensor, and
the server has the database and the advice creation section, wherein
the server transmits advice that has been created by the advice creation section to the imaging terminal, and this imaging terminal displays the advice on a display.

12. A server, comprising
a communication circuit for performing communication with a portable information terminal;
a database that stores health check results of the operator of the portable information terminal, and
a processor, wherein the processor
(1) receives bio-information of the operator from the portable information terminal via the communication circuit,
(2) determines causes of stress based on the relevancy between the bio-information that has been received and the health check results that have been stored in the database, and
(3) generates advice based on the causes of stress.

13. The server of claim 12, wherein:
the server transmits advice that has been created by the processor to the portable information terminal, and this portable information terminal displays the advice on a display.

* * * * *